(12) United States Patent
Humphries et al.

(10) Patent No.: US 11,136,303 B2
(45) Date of Patent: Oct. 5, 2021

(54) DIBENZOFURAN AND DIBENZOTHIOPHENE DERIVATIVES AND ORGANIC LIGHT-EMITTING DEVICES CONTAINING THEM

(71) Applicants: Cambridge Display Technology Limited, Godmanchester (GB); Sumitomo Chemical Company Limited, Tokyo (JP)

(72) Inventors: Martin Humphries, Godmanchester (GB); William Tarran, Godmanchester (GB); Kiran Kamtekar, Godmanchester (GB); Philip Stackhouse, Godmanchester (GB); James Lee, Godmanchester (GB)

(73) Assignees: Cambridge Display Technology Limited, Godmanchester (GB); Sumitomo Chemical Company Limited, Tokyo (JP)

(*) Notice: Subject to any disclaimer, the term of this patent is extended or adjusted under 35 U.S.C. 154(b) by 283 days.

(21) Appl. No.: 16/083,470

(22) PCT Filed: Mar. 7, 2017

(86) PCT No.: PCT/GB2017/050598
§ 371 (c)(1),
(2) Date: Sep. 7, 2018

(87) PCT Pub. No.: WO2017/153731
PCT Pub. Date: Sep. 14, 2017

(65) Prior Publication Data
US 2019/0084954 A1    Mar. 21, 2019

(30) Foreign Application Priority Data
Mar. 8, 2016    (GB) ..................... 1604002

(51) Int. Cl.
*C07D 307/91* (2006.01)
*C07D 333/76* (2006.01)
(Continued)

(52) U.S. Cl.
CPC ......... *C07D 307/91* (2013.01); *C07D 333/76* (2013.01); *C07F 7/0814* (2013.01);
(Continued)

(58) Field of Classification Search
CPC ... C07D 307/91; C07D 333/76; C07F 7/0814; H01L 51/0073; H01L 51/0074;
(Continued)

(56) References Cited

U.S. PATENT DOCUMENTS

2004/0124766 A1* 7/2004 Nakagawa .......... H01L 51/0073
313/504
2007/0224446 A1* 9/2007 Nakano ................ C07D 307/91
428/690
(Continued)

FOREIGN PATENT DOCUMENTS

EP    1 998 387 A1    12/2008
EP    2 001 064 A1    12/2008
(Continued)

OTHER PUBLICATIONS

Machine translation of WO 2010/004877 A1 (publication date Jan. 2010). (Year: 2010).*
(Continued)

*Primary Examiner* — Dawn L Garrett
(74) *Attorney, Agent, or Firm* — Wolf, Greenfield & Sacks, P.C.

(57) ABSTRACT

A compound of formula (I) wherein Z is a group of formula (II) and Core is selected from groups of formula (IIIa) or (IIIb) wherein X is S or O; $R^1$ is a substituent; n is 0 or a
(Continued)

positive integer; $Ar^1$ independently in each occurrence is an arylene group; $R^2$ is a substituent; $R^3$ is a substituent; $R^4$ is an arylene or heteroarylene group; Y is C or Si; a is 1, 2 or 3; b is 0 or a positive integer; and c is 0 or a positive integer. The compound of formula (I) may be used as a host for a light-emitting dopant in an organic light-emitting device.

Z-Core-Z (I)

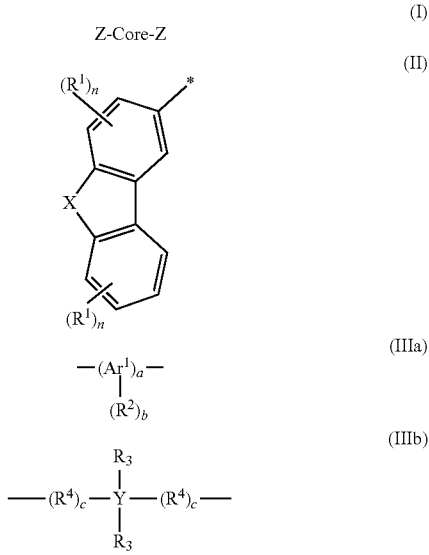

(II)

—$(Ar^1)_a$—
  |
  $(R^2)_b$ (IIIa)

$R_3$
 |
—$(R^4)_c$—Y—$(R^4)_c$—
 |
$R_3$ (IIIb)

20 Claims, 1 Drawing Sheet

(51) Int. Cl.
*H01L 51/00* (2006.01)
*H01L 51/50* (2006.01)
*C07F 7/08* (2006.01)

(52) U.S. Cl.
CPC ...... *H01L 51/0073* (2013.01); *H01L 51/0074* (2013.01); *H01L 51/0094* (2013.01); *H01L 51/504* (2013.01); *H01L 51/0085* (2013.01); *H01L 51/5016* (2013.01)

(58) Field of Classification Search
CPC ............. H01L 51/0085; H01L 51/0094; H01L 51/5016; H01L 51/504
See application file for complete search history.

(56) References Cited

U.S. PATENT DOCUMENTS

| | | | |
|---|---|---|---|
| 2009/0030202 A1 | 1/2009 | Iwakuma et al. | |
| 2009/0091253 A1* | 4/2009 | Yasukawa | H05B 33/20 313/504 |
| 2010/0084966 A1* | 4/2010 | Otsu | H01L 51/0073 313/504 |
| 2012/0061651 A1* | 3/2012 | Osaka | H01L 51/0074 257/40 |
| 2012/0068164 A1* | 3/2012 | Iwakuma | C07D 519/00 257/40 |
| 2013/0049576 A1* | 2/2013 | Katakura | H05B 33/20 313/504 |
| 2014/0183486 A1* | 7/2014 | Nakano | C07D 333/20 257/40 |
| 2016/0149139 A1* | 5/2016 | Xia | H01L 51/0061 257/40 |
| 2018/0375058 A1* | 12/2018 | Kawamura | H01L 51/5072 |

FOREIGN PATENT DOCUMENTS

| | | |
|---|---|---|
| EP | 2 034 538 A1 | 3/2009 |
| EP | 2 101 365 A1 | 9/2009 |
| EP | 2 166 583 A1 | 3/2010 |
| EP | 2 562 229 A1 | 2/2013 |
| EP | 2 711 363 A1 | 3/2014 |
| EP | 2 757 101 A1 | 7/2014 |
| EP | 2 781 347 A1 | 9/2014 |
| EP | 2 910 553 A1 | 8/2015 |
| KR | 2012-0129733 A | 11/2012 |
| WO | WO 2010/004877 A1 | 1/2010 |
| WO | WO 2014/042420 A | 3/2014 |
| WO | WO 2015/111864 A1 | 7/2015 |

OTHER PUBLICATIONS

PCT/GB2017/050598, Jul. 12, 2017, International Search Report and Written Opinion.
GB1604002.4, Dec. 22, 2016, Combined Search and Examination Report.
International Search Report and Written Opinion for International Application No. PCT/GB2017/050598, dated Jul. 12, 2017.
Combined Search and Examination Report for British Application No. GB1604002.4, dated Dec. 22, 2016.

* cited by examiner

DIBENZOFURAN AND DIBENZOTHIOPHENE DERIVATIVES AND ORGANIC LIGHT-EMITTING DEVICES CONTAINING THEM

RELATED APPLICATIONS

This Application is a national stage filing under 35 U.S.C. 371 of International Patent Application Serial No. PCT/GB2017/050598, filed Mar. 7, 2017, which claims priority to United Kingdom patent application GB 1604002.4, filed Mar. 8, 2016, each of which is incorporated herein by reference in its entirety.

FIELD OF THE INVENTION

The invention relates to compounds suitable for use as host materials for light-emitting dopants, in particular phosphorescent dopants, and organic light-emitting devices containing said compounds.

BACKGROUND OF THE INVENTION

Electronic devices containing active organic materials are attracting increasing attention for use in devices such as organic light emitting diodes (OLEDs), organic photoresponsive devices (in particular organic photovoltaic devices and organic photosensors), organic transistors and memory array devices. Devices containing active organic materials offer benefits such as low weight, low power consumption and flexibility. Moreover, use of soluble organic materials allows use of solution processing in device manufacture, for example inkjet printing or spin-coating.

An OLED may comprise a substrate carrying an anode, a cathode and one or more organic light-emitting layers between the anode and cathode.

Holes are injected into the device through the anode and electrons are injected through the cathode during operation of the device. Holes in the highest occupied molecular orbital (HOMO) and electrons in the lowest unoccupied molecular orbital (LUMO) of a light-emitting material combine to form an exciton that releases its energy as light.

Light-emitting materials include small molecule, polymeric and dendrimeric materials. Light-emitting polymers include poly(arylene vinylenes) such as poly(p-phenylene vinylenes) and polymers containing arylene repeat units, such as fluorene repeat units.

A light emitting layer may comprise a host material and a light-emitting dopant wherein energy is transferred from the host material to the light-emitting dopant. For example, J. Appl. Phys. 65, 3610, 1989 discloses a host material doped with a fluorescent light-emitting dopant (that is, a light-emitting material in which light is emitted via decay of a singlet exciton).

Phosphorescent dopants are also known (that is, a light-emitting dopant in which light is emitted via decay of a triplet exciton).

Sook et al, J. Mater. Chem., 2011, 21, 14604 discloses host materials DBT1, DBT2 and DBT3:

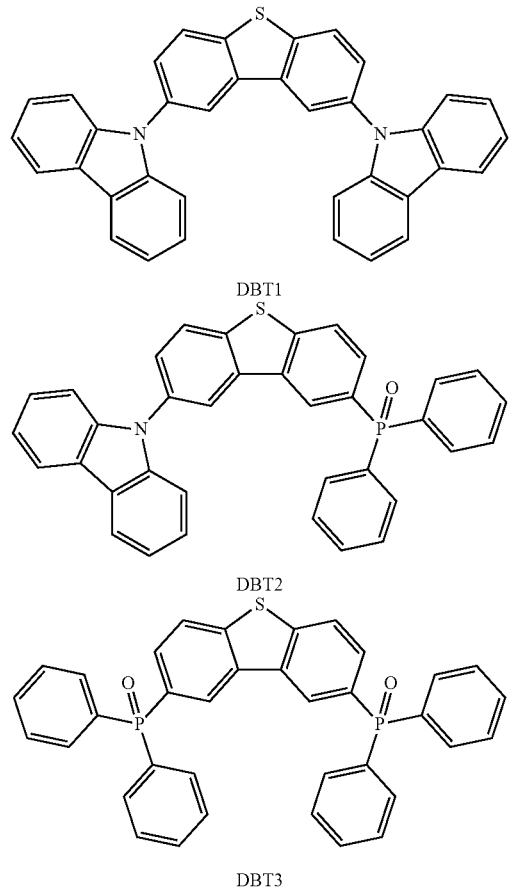

US 2009/167162 discloses dibenzothiophene-containing host compounds.

US 2013/0026909 discloses compounds of formula I:

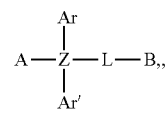

Formula I wherein Ar and Ar' are phenyl, biphenyl, naphthyl, dibenzothiophene and dibenzofuran, Z is Si or Ge; A is dibenzofuran, dibenzothiophene, azadibenzofuran, azadibenzothiophene, dibenzoselenophene or azadibenzoselenophene and B contains carbazole or azacarbazole.

WO 2012/162325 discloses compounds of formula I:

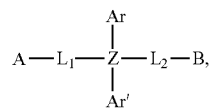

Formula I wherein Ar and Ar' are phenyl, biphenyl, naphthyl, dibenzothiolyl and dibenzofuranyl, Z is Si or Ge; L1 and L2 are aryl or nitrogen-containing heteroaryl; A is dibenzofuran, dibenzothiophene, azadibenzofuran, azadibenzothiophene, dibenzoselenophene or azadibenzoselenophene; and B contains carbazole orazacarbazole.

US 2015/069332 discloses compounds of formula:

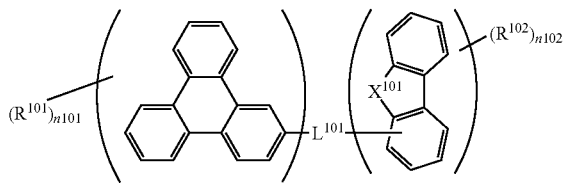

wherein $R^{101}$ and $R^{102}$ are certain substituents, $L^{101}$ represents a single bond or divalent linking group; $X^{101}$ is S or O; and one of $R^{101}$, $L^{101}$ and $R^{102}$ includes a fluorine atom, a fluoroalkyl group, a cycloalkyl group, a cycloalkylene group, a silyl group, an alkylsilyl group, an arylsilyl group or a silicon atom linking group.

US 2012/0319091 discloses a compound containing a group of formula:

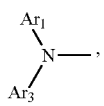

wherein Ar3 is a group of formula (4):

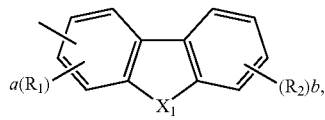

wherein X is O, S, NRa or CRbRc

JP 2007/126403 discloses compounds of formula (1):

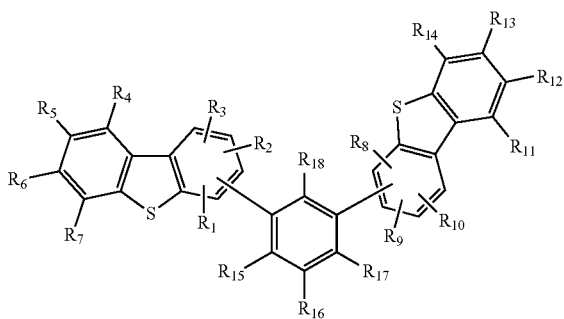

SUMMARY OF THE INVENTION

In a first aspect the invention provides a compound of formula (I):

Z-Core-Z           (I)

wherein:

Z in each occurrence is independently a group of formula (II):

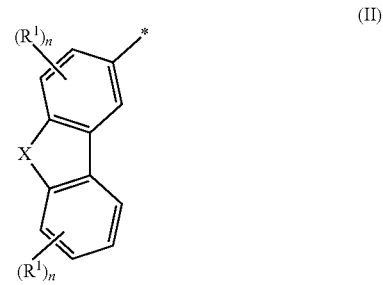

X is S or O;

$R^1$ independently in each occurrence is a substituent;

n is 0 or a positive integer;

-* is a direct bond to Core; and

Core is selected from groups of formula (IIIa) or (IIIb):

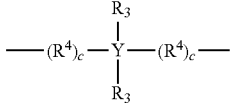

wherein $Ar^1$ independently in each occurrence is an arylene group; $R^2$ is a substituent; $R^3$ is a substituent; $R^4$ is an arylene or heteroarylene group that may independently in each occurrence be unsubstituted or substituted with one or more substituents; Y is C or Si; a is 1, 2 or 3; b independently in each occurrence is 0 or a positive integer; and c independently in each occurrence is 0 or a positive integer.

In a second aspect the invention provides a composition comprising a compound according to the first aspect and at least one light-emitting dopant.

In a third aspect the invention provides a formulation comprising a compound according to the first or second aspect or a composition according to the second aspect and one or more solvents.

In a fourth aspect the invention provides an organic light-emitting device comprising an anode, a cathode and a light-emitting layer between the anode and the cathode wherein the light-emitting layer comprises a compound according to the first aspect.

In a fifth aspect the invention provides a method of forming an organic light-emitting device according to the fourth aspect, the method comprising the step of forming the light-emitting layer over one of the anode and the cathode and forming the other of the anode and the cathode over the light-emitting layer.

"Aryl" and "heteroaryl" as used herein includes monocyclic and fused aryl and heteroaryl groups.

DESCRIPTION OF THE DRAWINGS

The invention will now be described in more detail with reference to the drawings in which.

DETAILED DESCRIPTION OF THE INVENTION

Figure 1:
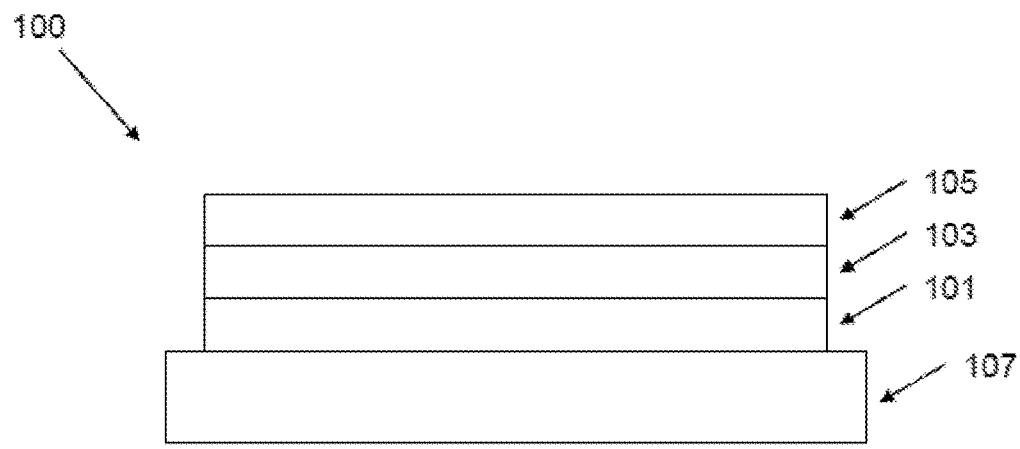
FIG. 1 illustrates an OLED according to an embodiment of the invention.

FIG. 1 illustrates an OLED 100 according to an embodiment of the invention comprising an anode 101, a cathode 105 and a light-emitting layer 103 between the anode and cathode. The device 100 is supported on a substrate 107, for example a glass or plastic substrate.

One or more further layers may be provided between the anode 101 and cathode 105, for example hole-transporting layers, electron transporting layers, hole blocking layers and electron blocking layers. The device may contain more than one light-emitting layer.

Preferred device structures include:
Anode/Hole-injection layer/Light-emitting layer/Cathode
Anode/Hole transporting layer/Light-emitting layer/Cathode
Anode/Hole-injection layer/Hole-transporting layer/Light-emitting layer/Cathode
Anode/Hole-injection layer/Hole-transporting layer/Light-emitting layer/Electron-transporting layer/Cathode
Anode/Hole-injection layer/Hole-transporting layer/Light-emitting layer/Hole-blocking layer/Electron-transporting layer/Cathode.

Preferably, at least one of a hole-transporting layer, hole injection layer, hole-blocking layer and electron-transporting layer is present. Preferably, both a hole injection layer and hole-transporting layer are present.

Light-emitting materials include red, green and blue light-emitting materials.

A blue emitting material may have a photoluminescent spectrum with a peak in the range of 400-490 nm, optionally 420-490 nm.

A green emitting material may have a photoluminescent spectrum with a peak in the range of more than 490 nm up to 580 nm, optionally more than 490 nm up to 540 nm.

A red emitting material may optionally have a peak in its photoluminescent spectrum of more than 580 nm up to 630 nm, optionally 585-625 nm.

The photoluminescence spectrum of a compound of formula (I) may be measured by casting 5 wt % of the material in a polystyrene film onto a quartz substrate and measuring in a nitrogen environment using apparatus C9920-02 supplied by Hamamatsu.

Light-emitting layer 103 contains a compound of formula (I) doped with one or more luminescent dopants. The light-emitting layer 103 may consist of these materials or may contain one or more further materials, for example one or more charge-transporting materials. When used as a host material for one or more light-emitting dopants, the lowest excited stated singlet ($S^1$) or the lowest excited state triplet ($T_1$) energy level of the compound of formula (I) is preferably no more than 0.1 eV below that of the light-emitting material, and is more preferably about the same as or higher than that of the light-emitting material in order to avoid quenching of luminescence from the light-emitting dopant.

In the case where the luminescent dopant is a phosphorescent dopant, the compound of formula (I) preferably has a $T_1$ of greater than 2.8 eV, preferably greater than 3.0 eV.

Triplet energy levels of compounds of formula (I) and phosphorescent materials may be measured from the energy onset of the phosphorescence spectrum measured by low temperature phosphorescence spectroscopy (Y. V. Romaovskii et al, Physical Review Letters, 2000, 85 (5), p 1027, A. van Dijken et al, Journal of the American Chemical Society, 2004, 126, p 7718).

The compounds of formula (I) preferably have a HOMO level of at least 5.8 eV from vacuum level, preferably at least 5.9 eV from vacuum level. HOMO and LUMO levels as given herein are as measured by square wave voltammetry.

In a preferred embodiment, light-emitting layer 103 contains a compound of formula (I) and at least one of green and blue phosphorescent light-emitting materials.

Compounds of Formula (I)

The compounds of formula (I) may have a Core group of formula (IIIa) or (IIIb).

The Core group is substituted with at least two groups of formula (II), denoted as groups Z in formula (I). The two groups Z may be the only groups of formula (II) in the compound of formula (I) or the compound may be substituted with one or more further groups of formula (II), optionally 1 or 2 further groups of formula (II), forming further groups Z.

In the case where Core is a group of formula (IIIa), each $Ar^1$ is preferably independently selected from $C_{6-20}$ arylene, more preferably phenyl.

The or each $Ar^1$ group may independently be unsubstituted or may be substituted with one or more groups $R^2$ wherein $R^2$ is a substituent. If there is more than one $Ar^1$ group then none, only one or more than one of the $Ar^1$ groups may be substituted.

The Core group of formula (IIIa) is preferably selected such that the extent of conjugation between groups Z of formula (I) is limited as compared to the case where Core is an unsubstituted 1,4-linked phenylene group.

The extent of conjugation may be limited by providing a substituent $R^2$ on one or more aromatic carbon atoms of an $Ar^1$ group adjacent to a bond linking the $Ar^1$ group to another $Ar^1$ group or to Z of formula (I).

At least one group $Ar^1$ may be a meta-linked arylene group, preferably meta-linked phenylene. Meta-linkage of an $Ar^1$ group may limit the extent of conjugation across Core as compared to the case where Core is an unsubstituted 1,4-linked phenylene group.

In the case where Core is a group of formula (IIIa) it is preferably selected from formulae (IIIa-1) and (IIIa-2):

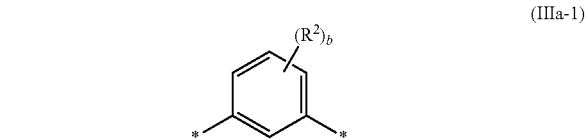

(IIIa-1)

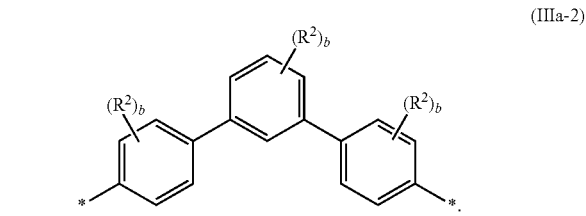

(IIIa-2)

Optionally each $R^2$, where present, is selected from the group consisting of:

branched, linear or cyclic $C_{1-20}$ alkyl wherein one or more non-adjacent, non-terminal C atoms of the $C_{1-20}$ alkyl may be replaced with O, S, CO or COO; and a group of formula (II).

b of formula (IIa-1) or (IIa-2) independently in each occurrence is 0, 1, 2, 3 or 4, preferably 0, 1 or 2.

By "non-terminal C atom" of an alkyl group as used herein means a methyl ($—CH_3$) group at the end of an n-alkyl chain or at each end of a branched alkyl chain.

Exemplary Core groups of formula (IIIa) include the following:

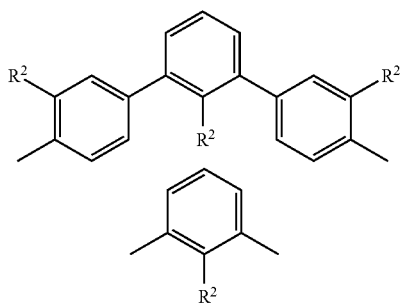

wherein $R^2$ independently in each occurrence is as described as above and is preferably $C_{1-20}$ alkyl, more preferably methyl.

In the case where Core is a group of formula (IIIb), $R^4$ is preferably a $C_{6-20}$ arylene group, preferably a phenylene group, which may be unsubstituted or substituted with one or more groups $R^5$, optionally 1, 2 or 3 groups $R^5$, wherein $R^5$ in each occurrence is a substituent.

Optionally each $R^5$, where present, is independently selected from branched, linear or cyclic $C_{1-12}$ alkyl wherein one or more non-adjacent, non-terminal C atoms of the $C_{1-12}$ alkyl group may be replaced with O, S, CO or COO; and a group of formula (II).

An aromatic carbon atom of a $C_{6-20}$ aryl group $R^4$ that is adjacent to the aromatic carbon bound to Z is preferably substituted with a substituent $R^5$, more preferably a $C_{1-12}$ alkyl group.

Each $R^3$, which may be the same or different in each occurrence, is optionally selected from the group consisting of:

- $C_{1-20}$ alkyl wherein one or more non-adjacent, non-terminal C atoms of the $C_{1-20}$ alkyl may be replaced with O, S, CO or COO;
- $C_{6-20}$ aryl, more preferably phenyl, which may be unsubstituted or substituted with one or more groups $R^6$ wherein each $R^6$ is independently a substituent; and
- a group of formula (II).

Each $R^6$ is independently selected from the group consisting of: D; F; CN; $C_{1-12}$ alkyl wherein one or more non-adjacent, non-terminal groups of the $C_{1-12}$ alkyl group may be replaced with O, S, CO or COO and one or more H atoms may be replaced with F; and a group of formula (II). If present, there may be 1-5 groups $R^6$.

In the case where an aromatic carbon atom of a $C_{6-20}$ aryl group $R^3$ is substituted with a group $R^6$ of formula (II), an adjacent carbon atom of the $C_{6-20}$ aryl group is preferably substituted with a different substituent R6, more preferably a $C_{1-12}$ alkyl substituent.

$R^3$ may comprise or consist of a group of formula (II).

In one preferred arrangement, each $R^3$ is phenyl which may independently be unsubstituted or substituted with one or more substituents $R^6$ wherein at least one substituent $R^6$ of at least one $R^3$ is a group of formula (II).

In another preferred arrangement, at least one $R^3$ is a group of formula (II):

In a yet further preferred arrangement, $R^3$ is phenyl which may independently be unsubstituted or substituted with one or more substituents $R^6$ other than a group of formula (II).

Each c of formula (IIIb) is preferably 0 or 1. Preferably, both c groups are either 0 or 1.

Core groups of formula (IIIb) are optionally selected from formulae (IIIb-1) and (IIIb-2):

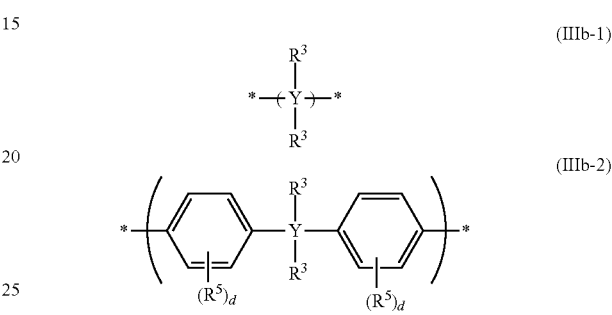

wherein d is 0, 1, 2, 3 or 4.

Optionally, n is 0, 1, 2 or 3, preferably 0 or 1.

Exemplary groups of formula (IIIb) include the following:

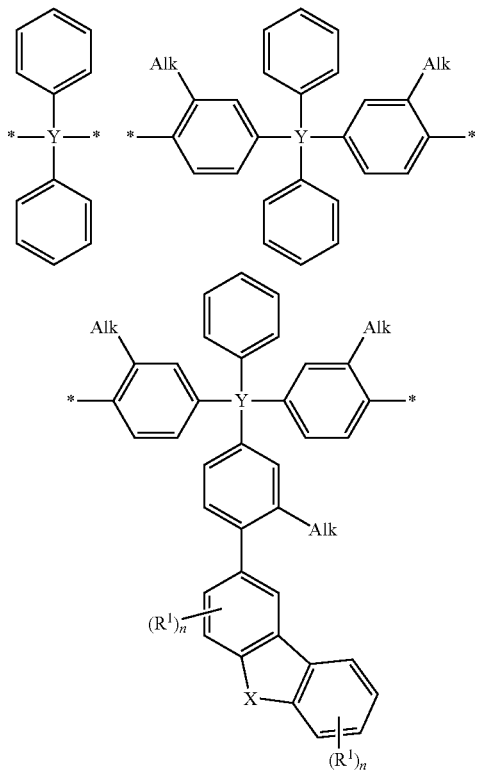

wherein Alk in each occurrence is a $C_{1-12}$ alkyl group, preferably methyl.

The groups Z of formula (II) may each independently be unsubstituted or substituted with one or more substituents $R^1$.

If present, R¹ in each occurrence is independently selected from:
- $C_{1-20}$ alkyl wherein one or more non-terminal, non-adjacent C atoms of the alkyl group may be replaced with O, S, CO or COO and one or more H atoms may be replaced with F, and
- $C_{6-20}$ aryl or 5-20 membered heteroaryl, preferably phenyl, which may be unsubstituted or substituted with one or more groups $R^7$ wherein each $R^7$ is independently a substituent.

$R^1$ is preferably selected from $C_{1-20}$ alkyl and phenyl which may be unsubstituted or substituted with one or more groups $R^7$.

Where present, each $R^7$ independently in each occurrence is optionally selected from $C_{1-12}$ alkyl wherein one or more non-terminal, non-adjacent C atoms of the alkyl group may be replaced with O, S, CO or COO and one or more H atoms may be replaced with F.

A substituent $R^7$ is preferably provided adjacent to a bond between an aryl or heteroaryl group $R^1$ and the group of formula (II) that $R^1$ is bound to.

Exemplary groups of formula (II) include the following:

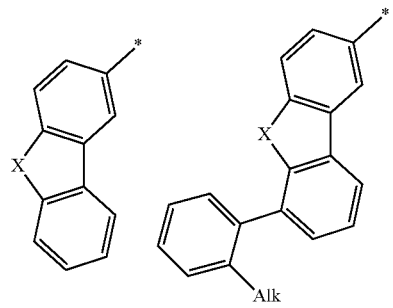

wherein Alk is $C_{1-12}$ alkyl.

Exemplary compounds of formula (I) are:

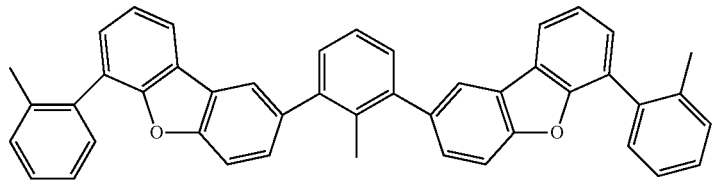

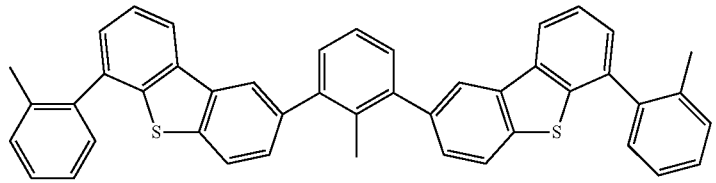

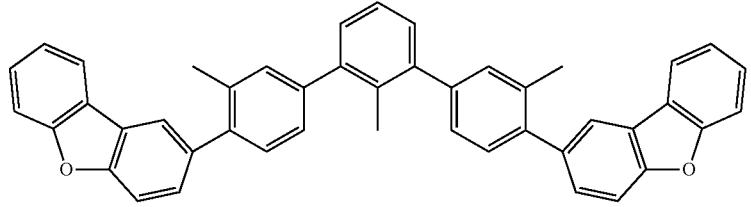

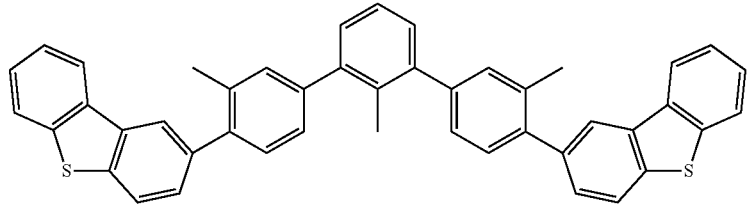

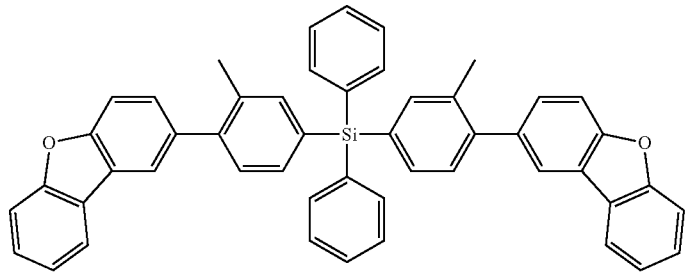

-continued
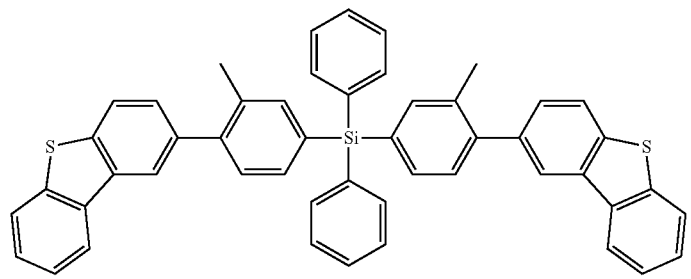
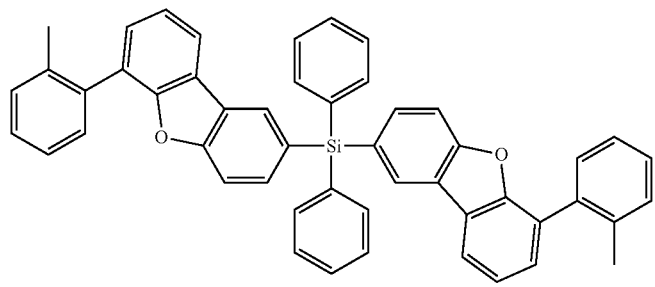
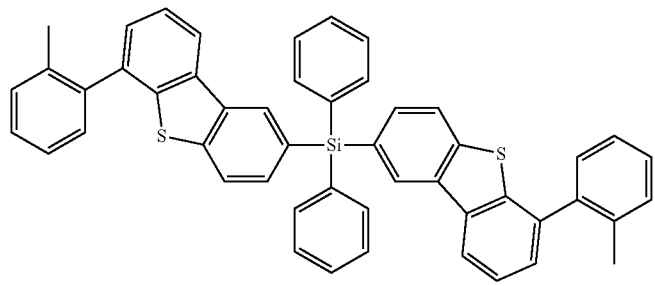
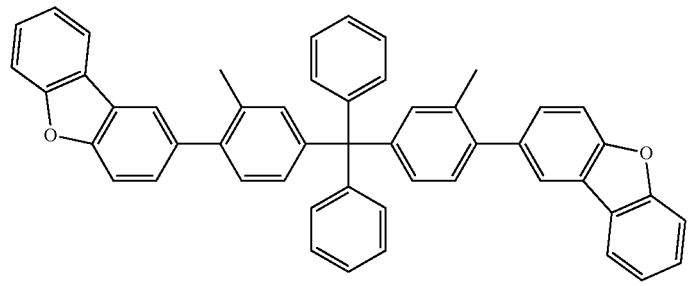
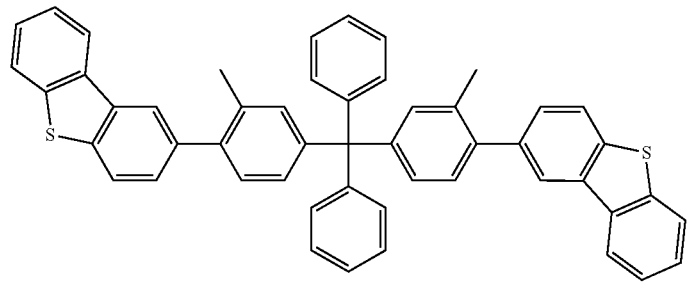
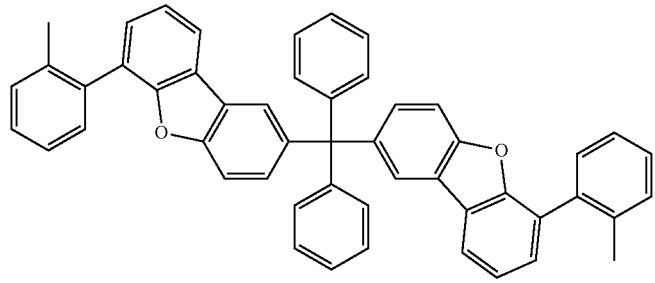

-continued
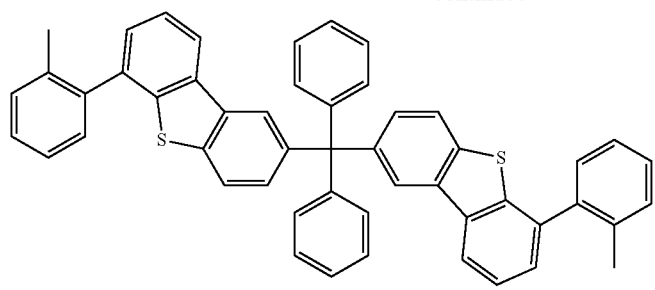
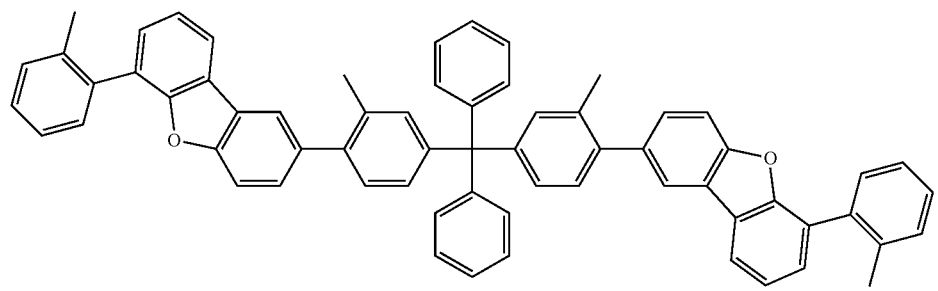
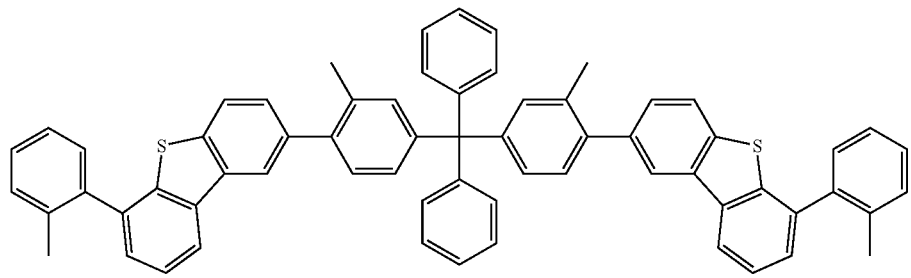
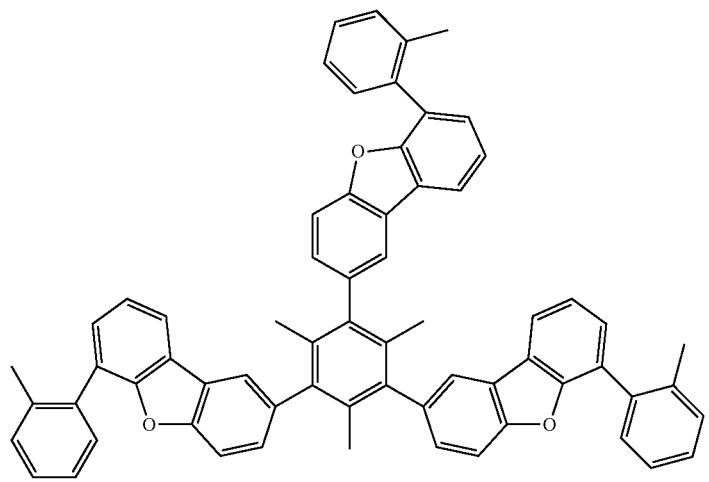

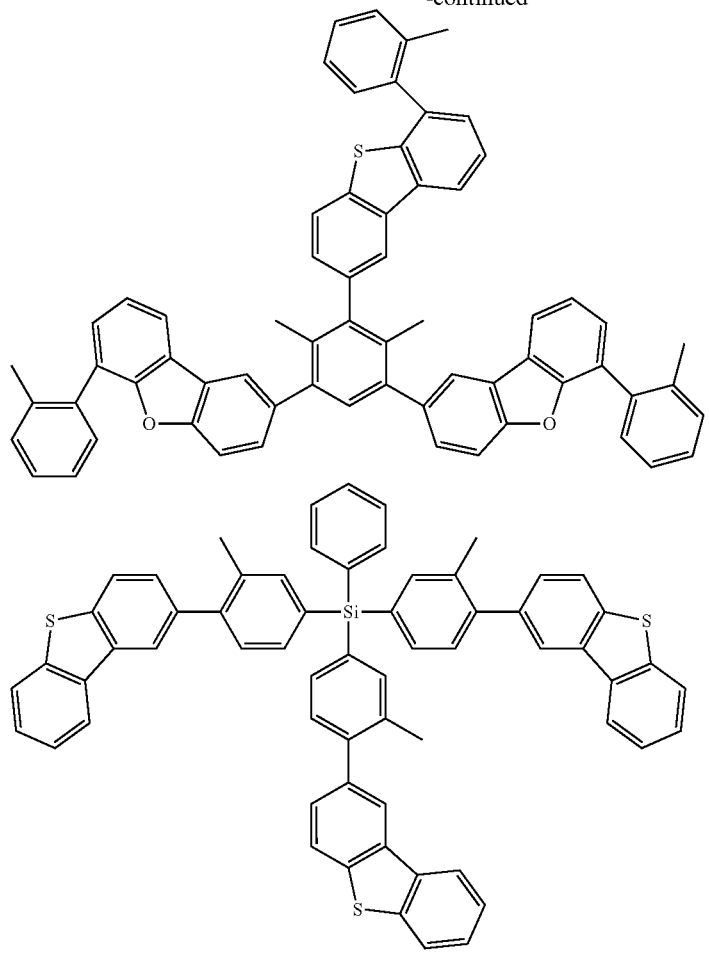

Light-Emitting Compounds

A preferred use of compounds of formula (I) is as the host material for a light-emitting material in a light-emitting layer of an OLED.

Suitable light-emitting materials for a light-emitting layer include polymeric, small molecule and dendritic light-emitting materials, each of which may be fluorescent or phosphorescent.

A light-emitting layer of an OLED may be unpatterned, or may be patterned to form discrete pixels. Each pixel may be further divided into subpixels. The light-emitting layer may contain a single light-emitting material, for example for a monochrome display or other monochrome device, or may contain materials emitting different colours, in particular red, green and blue light-emitting materials for a full-colour display.

A light-emitting layer may contain more than one light-emitting material, for example a mixture of light-emitting materials that together provide white light emission.

A white-emitting OLED may contain a single, white-emitting layer containing a light-emitting composition as described herein, or may contain two or more layers that emit different colours which, in combination, produce white light and wherein at least one of the light emitting layers comprises a composition as described herein.

The light emitted from a white-emitting OLED may have CIE x coordinate equivalent to that emitted by a black body at a temperature in the range of 2500-9000K and a CIE y coordinate within 0.05 or 0.025 of the CIE y co-ordinate of said light emitted by a black body, optionally a CIE x coordinate equivalent to that emitted by a black body at a temperature in the range of 2700-6000K.

Exemplary phosphorescent compounds have formula (IX):

$$ML^1_q L^2_r L^3_s \qquad (IX)$$

wherein M is a metal; each of $L^1$, $L^2$ and $L^3$ is a coordinating group that independently may be unsubstituted or substituted with one or more substituents; q is a positive integer; r and s are each independently 0 or a positive integer; and the sum of $(d·q)+(e·r)+(f·s)$ is equal to the number of coordination sites available on M, wherein d is the number of coordination sites on $L^1$, e is the number of coordination sites on $L^2$ and f is the number of coordination sites on $L^3$.

d, e and f are preferably each independently 1, 2 or 3. Preferably, $L^1$, $L^2$ and $L^3$ are each a bidentate ligand (d, e and f are each 2). In an embodiment, q is 3 and r and s are 0. In another embodiment, q is 1 or 2; r is 1; and s is 0 or 1, preferably 0.

Heavy elements M induce strong spin-orbit coupling to allow rapid intersystem crossing and emission from triplet or higher states. Suitable heavy metals M include d-block metals, in particular those in rows 2 and 3 i.e. elements 39 to 48 and 72 to 80, in particular ruthenium, rhodium, palladium, rhenium, osmium, iridium, platinum and gold. Iridium is particularly preferred.

Exemplary ligands $L^1$, $L^2$ and $L^3$ include carbon or nitrogen donors such as porphyrin or bidentate ligands of formula (X):

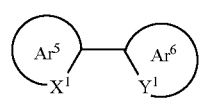
(X)

wherein $Ar^5$ and $Ar^6$ may be the same or different and are independently selected from substituted or unsubstituted aryl or heteroaryl; $X^1$ and $Y^1$ may be the same or different and are independently selected from carbon or nitrogen; and $Ar^5$ and $Ar^6$ may be fused together. Ligands wherein $X^1$ is carbon and $Y^1$ is nitrogen are preferred, in particular ligands in which $Ar^5$ is a single ring or fused heteroaromatic of N and C atoms only, for example pyridyl or isoquinoline, and $Ar^6$ is a single ring or fused aromatic, for example phenyl or naphthyl.

Each of $Ar^5$ and $Ar^6$ may carry one or more substituents. Two or more of these substituents may be linked to form a ring, for example an aromatic ring. Preferred substituents are selected from D, F, $C_{1-20}$ alkyl groups wherein one or more non-adjacent C atoms may be replaced with O, S, CO or COO and one or more H atoms may be replaced with F; phenyl or biphenyl that may be unsubstituted or substituted with one or more substituents, optionally one or more $C_1$-10 alkyl or $C_{1-12}$ alkoxy groups; and dendrons.

To achieve red emission, $Ar^5$ may be selected from phenyl, fluorene, naphthyl and $Ar^6$ are selected from quinoline, isoquinoline, thiophene and benzothiophene.

To achieve green emission, $Ar^5$ may be selected from phenyl or fluorene and $Ar^6$ may be pyridine.

To achieve blue emission, $Ar^5$ may be selected from phenyl and $Ar^6$ may be selected from imidazole, pyrazole, triazole and tetrazole.

Examples of bidentate ligands of formula (X) wherein $X^1$ is carbon and $Y^1$ is nitrogen are:

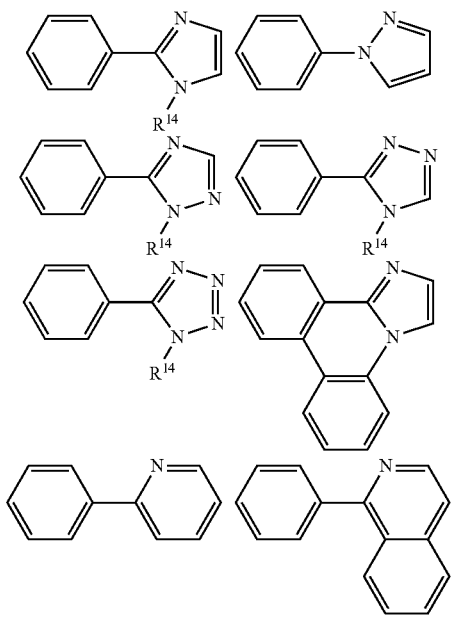

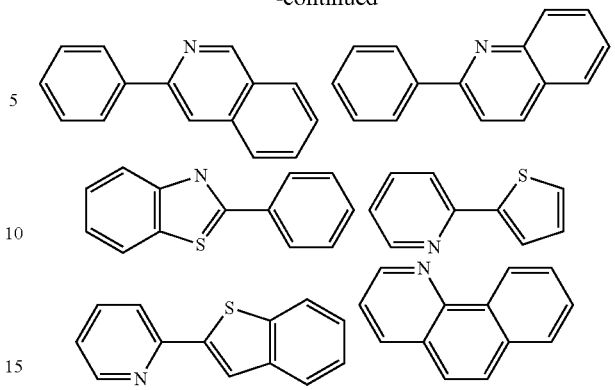

wherein $R^{14}$ is a substituent and wherein each C atom may independently be unsubstituted or substituted with a substituent $R^{15}$.

Substituents $R^{14}$ and $R^{15}$ are preferably selected from $C_{1-40}$ hydrocarbyl groups, preferably linear, branched or cyclic $C_{1-20}$ alkyl groups; phenyl or biphenyl which may be unsubstituted or substituted with one or more $C_{1-12}$ alkyl groups; and dendrons.

Other ligands suitable for use with d-block elements include O,O-bidentate ligands, optionally diketonates, O,N-bidentate ligands and N,N bidentate ligands, in particular acetylacetonate (acac), tetrakis-(pyrazol-1-yl)borate, 2-carboxypyridyl, triarylphosphines and pyridine, each of which may be substituted.

One or more of $L^1$, $L^2$ and $L^3$ may comprise a carbene group.

Preferably, compositions described herein comprise a compound of formula (I), preferably a phenylimidazole or phenyltriazole ligand and a blue phosphorescent material wherein:

q is 2 or 3 and each $L^1$ is a C,N-bidentate ligand of formula (X);

r is 0 or 1 and $L^2$, if present, is a C,N-bidentate ligand of formula (X) or an O,O-, N,N- or O,N-bidentate ligand;

s is 0;

and M is iridium.

Dendrons as described herein comprise a branching point attached to a ligand of the metal complex and two or more dendritic branches. Preferably, the dendron is at least partially conjugated, and at least one of the branching points and dendritic branches comprises an aryl or heteroaryl group, for example a phenyl group. In one arrangement, the branching point group and the branching groups are all phenyl, and each phenyl may independently be substituted with one or more substituents, for example $C_{1-20}$ alkyl or alkoxy.

A dendron may have optionally substituted formula (XI)

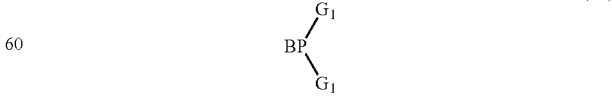
(XI)

wherein BP represents a branching point for attachment to a core and $G_1$ represents first generation branching groups.

The dendron may be a first, second, third or higher generation dendron. $G_1$ may be substituted with two or more second generation branching groups $G_2$, and so on, as in optionally substituted formula (XIa):

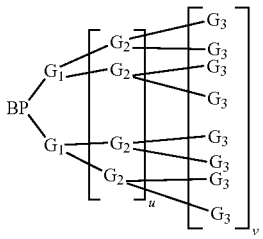

(XIa)

wherein u is 0 or 1; v is 0 if u is 0 or may be 0 or 1 if u is 1; BP represents a branching point for attachment to a core and $G_1$, $G_2$ and $G_3$ represent first, second and third generation dendron branching groups. In one preferred embodiment, each of BP and $G_1$, $G_2$ . . . $G_n$ is phenyl, and each phenyl BP, $G_1$, $G_2$ . . . $G_{n-1}$ is a 3,5-linked phenyl.

A preferred dendron is a substituted or unsubstituted dendron of formula (XIb):

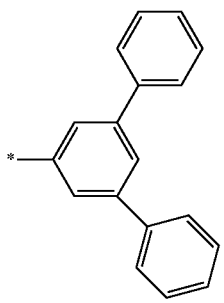

(XIb)

wherein * represents an attachment point of the dendron to a ligand.

BP and/or any group G may be substituted with one or more substituents, for example one or more $C_{1-20}$ alkyl or alkoxy groups.

Light-emitting material(s) in a composition comprising or consisting of the compound of formula (I) and one or more light-emitting materials may make up about 0.05 wt % up to about 50 wt %, optionally about 1-40 wt % of the composition.

Charge Transporting and Charge Blocking Layers

A device containing a light-emitting layer containing a compound of formula (I) may have charge-transporting and/or charge blocking layers.

A hole transporting layer may be provided between the anode and the light-emitting layer or layers of an OLED. An electron transporting layer may be provided between the cathode and the light-emitting layer or layers.

An electron blocking layer may be provided between the anode and the light-emitting layer(s) and a hole blocking layer may be provided between the cathode and the light-emitting layer(s). Charge-transporting and charge-blocking layers may be used in combination. Depending on the HOMO and LUMO levels of the material or materials in a layer, a single layer may both transport one of holes and electrons and block the other of holes and electrons.

If present, a hole transporting layer located between the anode and the light-emitting layer(s) preferably has a material having a HOMO level of less than or equal to 5.5 eV, more preferably around 4.8-5.5 eV or 4.9-5.3 eV as measured by square wave voltammetry. The HOMO level of the material in the hole transport layer may be selected so as to be within 0.2 eV, optionally within 0.1 eV of the light-emitting material of the light-emitting layer.

A hole-transporting layer may contain polymeric or non-polymeric charge-transporting materials. Exemplary hole-transporting materials contain arylamine groups.

A hole transporting layer may contain a homopolymer or copolymer comprising a repeat unit of formula (VII):

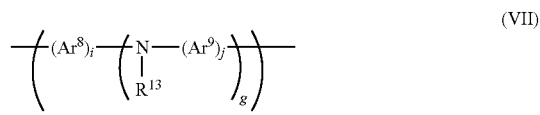

(VII)

wherein $Ar^8$ and $Ar^9$ in each occurrence are independently selected from substituted or unsubstituted aryl or heteroaryl, g is greater than or equal to 1, preferably 1 or 2, $R^{13}$ is H or a substituent, preferably a substituent, and i and j are each independently 1, 2 or 3, preferably 1 or 2.

$R^{13}$, which may be the same or different in each occurrence when g>1, is preferably selected from the group consisting of alkyl, for example $C_{1-20}$ alkyl, $Ar^{10}$, a branched or linear chain of $Ar^{10}$ groups, or a crosslinkable unit that is bound directly to the N atom of formula (VIII) or spaced apart therefrom by a spacer group, wherein $Ar^{10}$ in each occurrence is independently optionally substituted aryl or heteroaryl. Exemplary spacer groups are $C_{1-20}$ alkyl, phenyl and phenyl-$C_{1-20}$ alkyl.

Any of $Ar^8$, $Ar^9$ and, if present, $Ar^{10}$ in the repeat unit of Formula (VII) may be linked by a direct bond or a divalent linking atom or group to another of $Ar^8$, $Ar^9$ and $Ar^{10}$. Preferred divalent linking atoms and groups include O, S; substituted N; and substituted C.

Any of $Ar^8$, $Ar^9$ and, if present, $Ar^{10}$ may be substituted with one or more substituents. Exemplary substituents are substituents $R^{10}$, wherein each $R^{10}$ may independently be selected from the group consisting of:

substituted or unsubstituted alkyl, optionally $C_{1-20}$ alkyl, wherein one or more non-adjacent C atoms may be replaced with optionally substituted aryl or heteroaryl, O, S, substituted N, C=O or —COO— and one or more H atoms may be replaced with F; and a crosslinkable group attached directly to $Ar^8$, $Ar^9$ or $Ar^{10}$ or spaced apart therefrom by a spacer group, for example a group comprising a double bond such and a vinyl or acrylate group, or a benzocyclobutane group Preferred repeat units of formula (VII) have formulae 1-3:

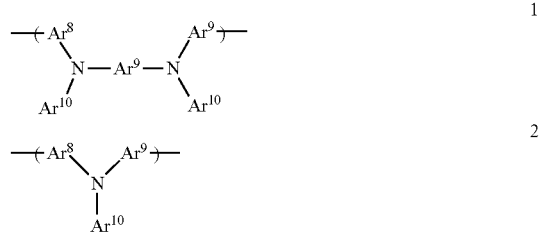

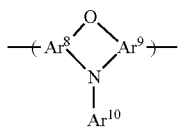

In one preferred arrangement, $R^{13}$ is $Ar^{10}$ and each of $Ar^8$, $Ar^9$ and $Ar^{10}$ are independently and optionally substituted with one or more $C_{1-20}$ alkyl groups. $Ar^8$, $Ar^9$ and $Ar^{10}$ are preferably phenyl.

In another preferred arrangement, the central $Ar^9$ group of formula (1) linked to two N atoms is a polycyclic aromatic that may be unsubstituted or substituted with one or more substituents $R^{10}$. Exemplary polycyclic aromatic groups are naphthalene, perylene, anthracene and fluorene.

In another preferred arrangement, $Ar^8$ and $Ar^9$ are phenyl, each of which may be substituted with one or more $C_{1-20}$ alkyl groups, and $R^{13}$ is $—(Ar^{10})_r$ wherein r is at least 2 and wherein the group $—(Ar^{10})_r$ forms a linear or branched chain of aromatic or heteroaromatic groups, for example 3,5-diphenylbenzene wherein each phenyl may be substituted with one or more $C_{1-20}$ alkyl groups. In another preferred arrangement, c, d and g are each 1 and $Ar^8$ and $Ar^9$ are phenyl linked by an oxygen atom to form a phenoxazine ring.

A hole-transporting polymer containing repeat units of formula (VII) may be a copolymer containing one or more further repeat units. Exemplary further repeat units include arylene repeat units, each of which may be unsubstituted or substituted with one or more substituents.

Exemplary arylene repeat units include without limitation, fluorene, phenylene, naphthalene, anthracene, indenofluorene, phenanthrene and dihydrophenanthrene repeat units, each of which may be unsubstituted or substituted with one or more substituents.

Substituents of arylene repeat units, if present, may be selected from $C_{1-40}$ hydrocarbyl, preferably $C_{1-20}$ alkyl; phenyl which may be unsubstituted or substituted with one or more $C_{1-10}$ alkyl groups; and crosslinkable hydrocarbyl groups, for example $C_{1-40}$ hydrocarbyl groups comprising benzocyclobutene or vinylene groups.

Phenylene repeat units may be 1,4-linked phenylene repeat units that may be unsubstituted or substituted with 1, 2, 3 or 4 substituents. Fluorene repeat units may be 2,7-linked fluorene repeat units.

Fluorene repeat units preferably have two substituents in the 9-position thereof.

Aromatic carbon atoms of fluorene repeat units may each independently be unsubstituted or substituted with a substituent.

If present, an electron transporting layer located between the light-emitting layers and cathode preferably has a LUMO level of around 1.8-2.7 eV as measured by square wave voltammetry. An electron-transporting layer may have a thickness in the range of about 5-50 nm.

If present, a hole-blocking layer may comprise or consist of a compound of formula (XII):

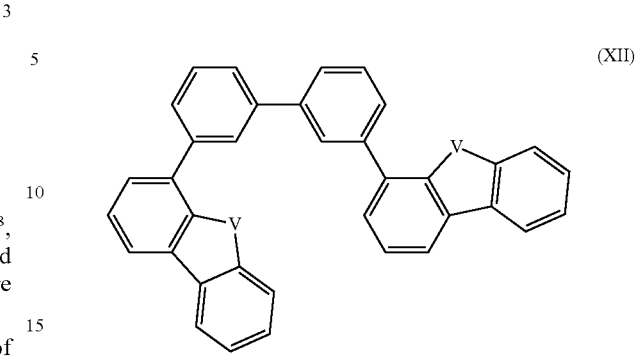

wherein V in each occurrence is independently S or O, preferably S. The compound of formula (XII) may be unsubstituted or may be substituted with one or more substituents, optionally one or more $C_{1-40}$ hydrocarbyl groups, optionally one or more $C_{1-20}$ alkyl groups.

A charge-transporting layer or charge-blocking layer may be crosslinked, particularly if a layer overlying that charge-transporting or charge-blocking layer is deposited from a solution. The crosslinkable group used for this crosslinking may be a crosslinkable group comprising a reactive double bond such and a vinyl or acrylate group, or a benzocyclobutane group. The crosslinkable group may be provided as a substituent of, or may be mixed with, a charge-transporting or charge-blocking material used to form the charge-transporting or charge-blocking layer.

A charge-transporting layer adjacent to a light-emitting layer containing a phosphorescent light-emitting material preferably contains a charge-transporting material having a lowest triplet excited state ($T_1$) excited state that is no more than 0.1 eV lower than, preferably the same as or higher than, the $T_1$ excited state energy level of the phosphorescent light-emitting material(s) in order to avoid quenching of triplet excitons.

A charge-transporting layer as described herein may be non-emissive, or may contain a light-emitting material such that the layer is a charge transporting light-emitting layer. If the charge-transporting layer is a polymer then a light-emitting dopant may be provided as a side-group of the polymer, a repeat unit in a backbone of the polymer, or an end group of the polymer. Optionally, a hole-transporting polymer as described herein comprises a phosphorescent polymer in a side-group of the polymer, in a repeat unit in a backbone of the polymer, or as an end group of the polymer.

The polystyrene-equivalent number-average molecular weight (Mn) measured by gel permeation chromatography of the polymers described herein may be in the range of about $1 \times 10^3$ to $1 \times 10^8$, and preferably $1 \times 10^4$ to $5 \times 10^6$. The polystyrene-equivalent weight-average molecular weight (Mw) of the polymers described herein may be $1 \times 10^3$ to $1 \times 10^8$, and preferably $1 \times 10^4$ to $1 \times 10^7$.

Polymers as described herein are suitably amorphous.

Hole Injection Layers

A conductive hole injection layer, which may be formed from a conductive organic or inorganic material, may be provided between the anode 101 and the light-emitting layer 103 of an OLED as illustrated in FIG. 1 to assist hole injection from the anode into the layer or layers of semiconducting polymer. Examples of doped organic hole injection materials include optionally substituted, doped poly (ethylene dioxythiophene) (PEDOT), in particular PEDOT doped with a charge-balancing polyacid such as polystyrene sulfonate (PSS) as disclosed in EP 0901176 and EP 0947123, polyacrylic acid or a fluorinated sulfonic acid, for example Nafion®; polyaniline as disclosed in U.S. Pat. Nos. 5,723,873 and 5,798,170; and optionally substituted polythiophene or poly(thienothiophene). Examples of conductive inorganic materials include transition metal oxides such as VOx, MoOx and RuOx as disclosed in Journal of Physics D: Applied Physics (1996), 29(11), 2750-2753.

Cathode

The cathode 105 is selected from materials that have a work function allowing injection of electrons into the light-emitting layer of the OLED. Other factors influence the selection of the cathode such as the possibility of adverse interactions between the cathode and the light-emitting material. The cathode may consist of a single material such as a layer of aluminium. Alternatively, it may comprise a plurality of conductive materials such as metals, for example a bilayer of a low work function material and a high work function material such as calcium and aluminium, for example as disclosed in WO 98/10621. The cathode may comprise elemental barium, for example as disclosed in WO 98/57381, Appl. Phys. Lett. 2002, 81(4), 634 and WO 02/84759. The cathode may comprise a thin (e.g. 1-5 nm) layer of metal compound, in particular an oxide or fluoride of an alkali or alkali earth metal, between the organic layers of the device and one or more conductive cathode layers to assist electron injection, for example lithium fluoride as disclosed in WO 00/48258; barium fluoride as disclosed in Appl. Phys. Lett. 2001, 79(5), 2001; and barium oxide. In order to provide efficient injection of electrons into the device, the cathode preferably has a work function of less than 3.5 eV, more preferably less than 3.2 eV, most preferably less than 3 eV. Work functions of metals can be found in, for example, Michaelson, J. Appl. Phys. 48(11), 4729, 1977.

The cathode may be opaque or transparent. Transparent cathodes are particularly advantageous for active matrix devices because emission through a transparent anode in such devices is at least partially blocked by drive circuitry located underneath the emissive pixels. A transparent cathode comprises a layer of an electron injecting material that is sufficiently thin to be transparent. Typically, the lateral conductivity of this layer will be low as a result of its thinness. In this case, the layer of electron injecting material is used in combination with a thicker layer of transparent conducting material such as indium tin oxide.

It will be appreciated that a transparent cathode device need not have a transparent anode (unless, of course, a fully transparent device is desired), and so the transparent anode used for bottom-emitting devices may be replaced or supplemented with a layer of reflective material such as a layer of aluminium. Examples of transparent cathode devices are disclosed in, for example, GB 2348316.

Encapsulation

Organic optoelectronic devices tend to be sensitive to moisture and oxygen.

Accordingly, the substrate preferably has good barrier properties for prevention of ingress of moisture and oxygen into the device. The substrate is commonly glass, however alternative substrates may be used, in particular where flexibility of the device is desirable. For example, the substrate may comprise one or more plastic layers, for example a substrate of alternating plastic and dielectric barrier layers or a laminate of thin glass and plastic.

The device may be encapsulated with an encapsulant (not shown) to prevent ingress of moisture and oxygen. Suitable encapsulants include a sheet of glass, films having suitable barrier properties such as silicon dioxide, silicon monoxide, silicon nitride or alternating stacks of polymer and dielectric or an airtight container. In the case of a transparent cathode device, a transparent encapsulating layer such as silicon monoxide or silicon dioxide may be deposited to micron levels of thickness, although in one preferred embodiment the thickness of such a layer is in the range of 20-300 nm. A getter material for absorption of any atmospheric moisture and/or oxygen that may permeate through the substrate or encapsulant may be disposed between the substrate and the encapsulant.

Formulation Processing

A formulation suitable for forming a charge-transporting or light-emitting layer may be formed from a compound of formula (I), any further components of the layer such as light-emitting dopants, and one or more suitable solvents.

The formulation may be a solution of the compound of formula (I) and any other components in the one or more solvents, or may be a dispersion in the one or more solvents in which one or more components are not dissolved. Preferably, the formulation is a solution.

Solvents suitable for dissolving compounds of formula (I) are benzenes substituted with one or more $C_{1-10}$ alkyl or $C_{1-10}$ alkoxy groups, for example toluene, xylenes and methylanisoles.

Particularly preferred solution deposition techniques including printing and coating techniques such spin-coating, inkjet printing and slot-die coating.

Spin-coating is particularly suitable for devices wherein patterning of the light-emitting layer is unnecessary—for example for lighting applications or simple monochrome segmented displays.

Inkjet printing is particularly suitable for high information content displays, in particular full colour displays. A device may be inkjet printed by providing a patterned layer over the first electrode and defining wells for printing of one colour (in the case of a monochrome device) or multiple colours (in the case of a multicolour, in particular full colour device). The patterned layer is typically a layer of photoresist that is patterned to define wells as described in, for example, EP 0880303.

As an alternative to wells, the ink may be printed into channels defined within a patterned layer. In particular, the photoresist may be patterned to form channels which, unlike wells, extend over a plurality of pixels and which may be closed or open at the channel ends.

Other solution deposition techniques include dip-coating, roll printing and screen printing.

EXAMPLES

Intermediate A

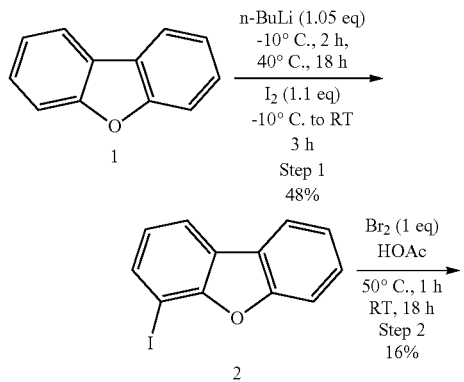

-continued

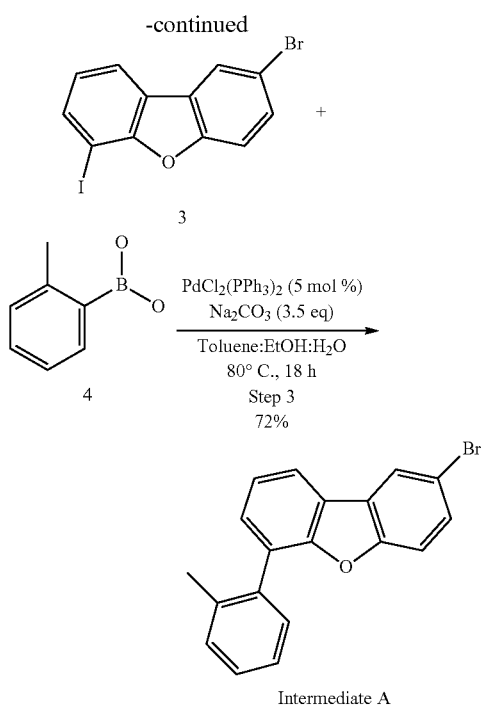

Intermediate A

Step 1—Synthesis of Intermediate 2

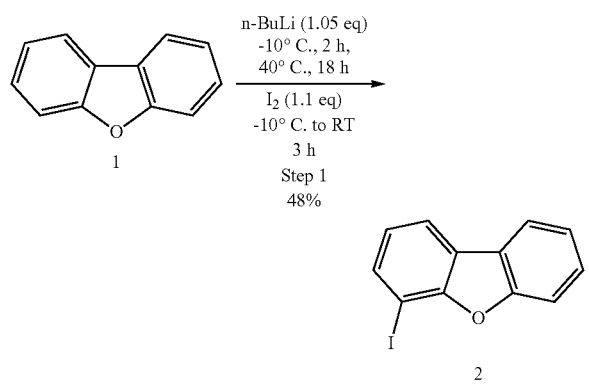

| Reagent | Quantity (g) | Vol. (mL) | MW | Moles | Eq |
|---|---|---|---|---|---|
| Dibenzofuran | 300 | | 168.2 | 1.7836 | 1 |
| n-BuLi (2.5M in hexane) | | 749 | | 1.872 | 1.05 |
| Iodine | 498.1 | | 253.9 | 1.9619 | 1.1 |
| Diethyl ether | | 3000 | | | |

Apparatus Set-Up:

A 10 L 3-necked round-bottomed flask, equipped with a mechanical overhead stirrer, reflux condenser, nitrogen inlet and exhaust.

Experimental Procedure:

Dibenzofuran (300 g, 1.7836 mol) was taken in dry diethyl ether (3 L).

The reaction mixture was cooled to −10° C. and 2.5M n-BuLi in hexane (749 mL, 1.872 mol) was slowly added.

The reaction mixture was warmed to 40° C. and stirred for 18 h.

The mixture was again cooled to −10° C. and iodine (498.1 g, 1.9619 mol) was added portion wise slowly.

The reaction mixture was allowed to warm to room temperature and stirred for 3 h.

The reaction mixture was quenched with water (500 mL) and extracted with diethyl ether (2×1 L).

The combined organic phase was washed with sodium thiosulphate solution (500 g in 2 L of water), water (1 L), brine (1 L), dried over sodium sulphate and concentrated.

The crude product (320 g) was purified by hot acetonitrile to get 310 g of intermediate 2 with 90% HPLC purity, then taken again in hot hexane and cooled to room temperature (2 times) to get 250 g of intermediate 2 with 98.75% HPLC purity.

$^1$H-NMR (400 MHz, CDCl$_3$): δ [ppm] δ 7.11-7.16 (m, 1H), 7.29-7.42 (m, 1H), 7.50-7.54 (m, 1H), 7.67-7.70 (m, 1H), 7.82-7.85 (m, 1H), 7.91-7.96 (m, 2H).

Step 2—Synthesis of Intermediate 3

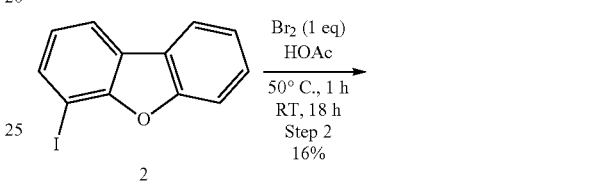

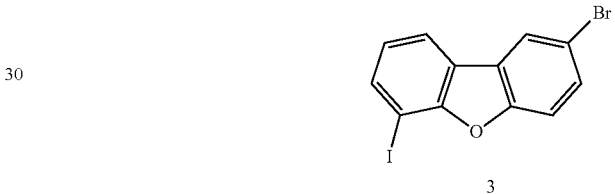

| Reagent | Quantity (g) | Vol. (mL) | MW | Moles | Eq. |
|---|---|---|---|---|---|
| Intermediate 2 | 250 | | 294.09 | 0.8501 | 1 |
| Bromine | 135.85 | 43.8 | 159.81 | 0.8501 | 1 |
| CH$_3$COOH | | 2500 | | | |

Apparatus Set-Up:

A 5 L 3-necked round-bottomed flask, equipped with a mechanical overhead stirrer, reflux condenser, nitrogen inlet and exhaust.

Experimental Procedure:

Intermediate 2 (250 g, 0.8501 mol) was taken in acetic acid (2.5 L).

The mixture was heated to 55° C. and bromine (43.8 mL, 0.8501 mol) was slowly added.

After complete the addition, it was stirred at 55° C. for an hour.

The mixture was stirred at room temperature for 18 h.

After 18 hours, the reaction mixture was filtered and the solid was washed with 10% sodium thiosulfate solution (1 L), water (1 L) to get 120 g of crude product.

The crude product was triturated with diethyl ether and filtered to get 95 g of intermediate 3 with 87% HPLC purity.

It was further purified by hot acetonitrile crystallization (3 times) and filtered to get 50 g of intermediate 3 with 94.78% HPLC purity.

$^1$H-NMR (400 MHz, CDCl$_3$): δ [ppm] 7.12-7.16 (m, 1H), 7.54 (d, J=8.8 Hz, 1H), 7.59 (dd, J=2.0 Hz, 8.8 Hz, 1H), 7.85-7.89 (m, 2H), 7.54 (d, J=8.8 Hz, 1H).

Step 3—Synthesis of Intermediate A

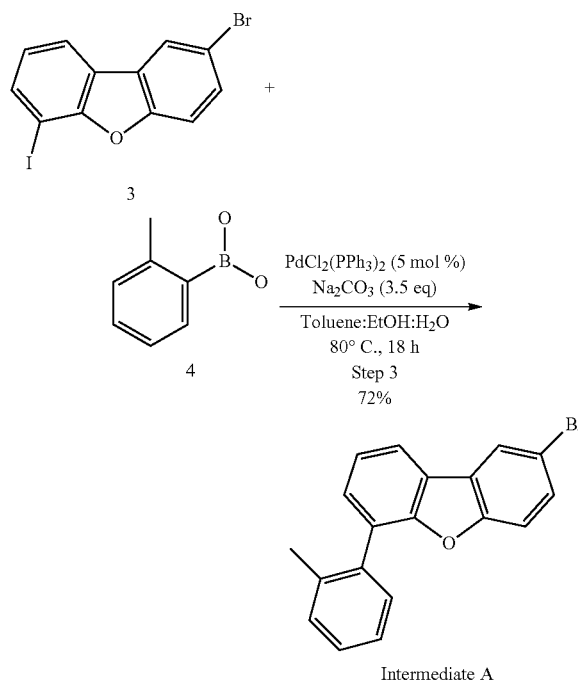

| Reagent | Quantity (g) | Vol. (mL) | MW | Moles | Eq. |
|---|---|---|---|---|---|
| Intermediate 3 | 50 | | 372.99 | 0.134 | 1 |
| Intermediate 4 | 18.2 | | 135.95 | 0.134 | 1 |
| Sodium carbonate | 49.7 | | 105.98 | 0.469 | 3.5 |
| PdCl$_2$(PPh$_3$)$_2$ | 4.7 | | 701.90 | 0.0067 | 0.05 |
| Toluene:EtOH:water (1:1:0.5) | | 625 | | | |

Apparatus Set-Up:

A 2 L 3-necked round-bottomed flask, equipped with a mechanical overhead stirrer, reflux condenser, nitrogen inlet and exhaust.

Experimental Procedure:

Intermediate 3 (50 g, 0.134 mol) and 2-methyl phenyl boronic acid (18.2 g, 0.134 mol) were taken in toluene (250 mL) and ethanol (250 mL).

Sodium carbonate solution (49.7 g, 0.469 mol, dissolved in 125 mL of water) was added.

The reaction mixture was degassed with nitrogen for an hour.

PdCl$_2$ (PPh$_3$)$_2$ (4.7 g, 0.0067 mol) was added and heated at 80° C. for 16 h.

After completion of the reaction, the mixture was filtered through a Florosil-silica plug and concentrated.

The residue was dissolved in ethyl acetate (1 L), washed with water (500 mL), brine (500 mL), dried over sodium sulphate and concentrated.

The crude product (65 g) was purified by silica column chromatography using 5% ethyl acetate in hexane as an eluent to get 52 g of Intermediate A with 91% HPLC purity.

52 g of Intermediate A was again purified by Combi-flash column chromatography using 2% ethyl acetate in hexane as an eluent to get 40 g of Intermediate A with 91% HPLC purity.

This was again purified by reverse phase column chromatography (5 g×8 runs) using 100% acetonitrile as an eluent to get Fraction 1: 29 g with 97% HPLC purity Fraction 2: 8 g with 92% HPLC purity.

All the fractions were combined and purified by Combi flash column chromatography using only hexane for elution to get 32.5 g of Intermediate A with 99.80% HPLC purity. The material was dissolved in hexane (500 mL), heated to 50° C., filtered the hot solution and concentrated to get 32.5 g of Intermediate A as viscous oil.

$^1$H-NMR (400 MHz, CDCl$_3$): δ [ppm] 2.26 (s, 3H), 7.34-7.47 (m, 7H), 7.54 (dd, J=1.6 Hz, 6.4 Hz, 1H), 7.93 (dd, J=1.6 Hz, 7.2 Hz, 1H), 8.13 (d, J=1.6 Hz, 1H).

Intermediate B

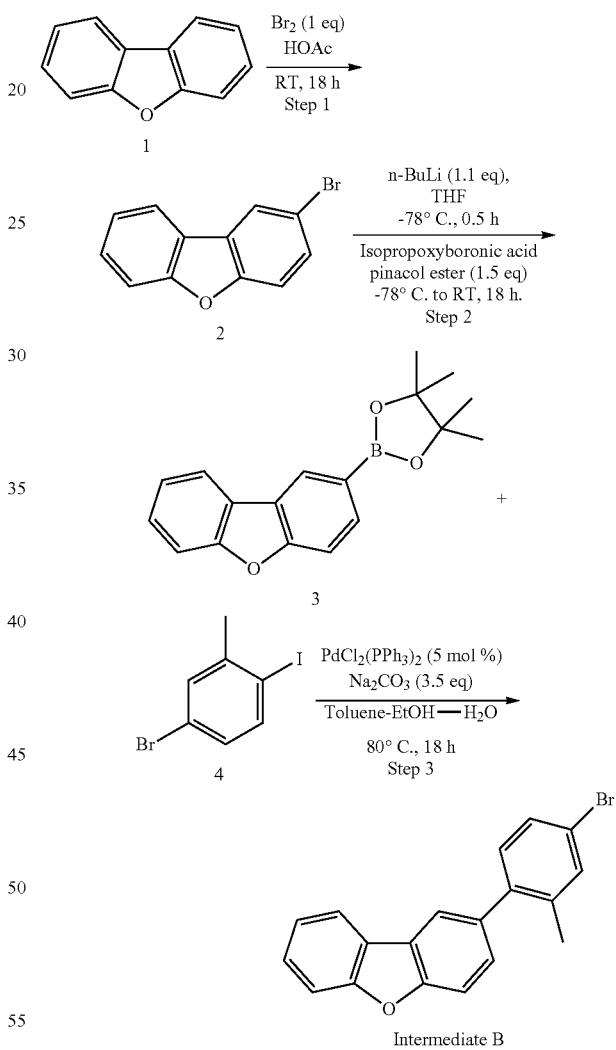

Step 1—Synthesis of Intermediate 2

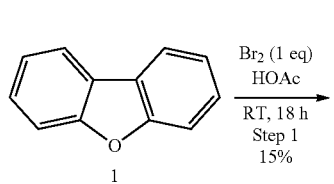

-continued

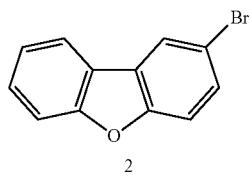

2

| Reagent | Quantity (g) | Vol. (mL) | MW | Moles | Eq |
|---|---|---|---|---|---|
| Dibenzofuran | 300 | | 168.2 | 1.783 | 1 |
| Bromine | 284.9 | 91.9 | 159.8 | 1.783 | 1 |
| Acetic acid | | 2000 | | | |

Apparatus Set-Up:

A 10 L 3-necked round-bottomed flask, equipped with a mechanical overhead stirrer, reflux condenser, nitrogen inlet and exhaust.

Experimental Procedure:

Dibenzofuran (300 g, 1.783 mol) was taken in acetic acid (2 L) and heated to 45° C. for 30 min to obtain a clear solution.

The mixture was allowed to room temperature and bromine (91.9 mL, 1.783 mol) was slowly added.

The reaction mixture was stirred at room temperature for 18 h.

The reaction mixture was filtered, washed with water (1 L) and dried.

The solid obtained was dissolved in ethyl acetate (4 L), washed with sodium thiosulphate solution (1 Kg in 3 L of water), water (1 L), dried over sodium sulphate and concentrated to get 148 g of crude product.

The crude product (148 g) was purified by hot toluene/methanol crystallization to get 102 g of intermediate 2, taken again in hot ethyl acetate/hexane and cooled to room temperature to get 76 g of intermediate 2.

Another 65 g of intermediate 2 was prepared from 300 g of dibenzofuran.

Both fractions (76 g+65 g) were combined and purified again with hot ethyl acetate/hexane to get 110 g of intermediate 2 with 98.89% HPLC purity.

$^1$H-NMR (400 MHz, CDCl$_3$): δ [ppm] δ 7.36-7.40 (m, 1H), 7.46 (d, J=8.8 Hz, 1H), 7.49-7.53 (m, 1H), 7.55-7.60 (m, 2H), 7.92 (dd, J=2.0 Hz, 7.6 Hz, 1H), 8.09 (d, J=2.0 Hz, 1H).

Step 2—Synthesis of Intermediate 3

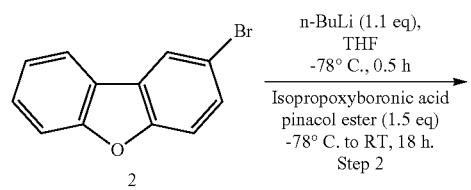

-continued

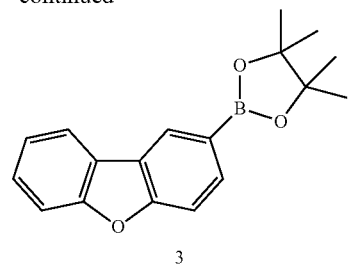

3

| Reagent | Quantity (g) | Vol. (mL) | MW | Moles | Eq. |
|---|---|---|---|---|---|
| Intermediate 2 | 110 | | 247.09 | 0.445 | 1 |
| 2.5M n-BuLi in hexane | | 195.8 | | 0.489 | 1.1 |
| Isopropoxy boronic acid pinacol ester | 124.2 | 132.1 | 186.06 | 0.667 | 1.5 |
| THF | | 2500 | | | |

Apparatus Set-Up:

A 5 L 3-necked round-bottomed flask, equipped with a mechanical overhead stirrer, nitrogen inlet and exhaust.

Experimental Procedure:

Intermediate 2 (110 g, 0.445 mol) was taken in THF (2.5 L) and cooled to −78° C. using dry ice/acetone bath.

2.5M n-BuLi in hexane (195.8 mL, 0.489 mol) was slowly added.

The mixture was stirred at −78° C. for 30 min for complete lithiation.

Isopropoxy boronic acid pinacol ester (132.1 mL, 0.667 mol) was slowly added.

After completing the addition, the mixture was allowed to room temperature and stirred for 18 h.

After 18 h, the reaction mixture was quenched with aqueous NH$_4$Cl solution (100 mL) and extracted with ethyl acetate (2 L).

The combined organic phase was washed with water (1 L), brine (1 L) dried over sodium sulphate and concentrated to get 135 g of crude product.

The crude product was an oil that was used directly in the next step.

Step 3—Synthesis of Intermediate B

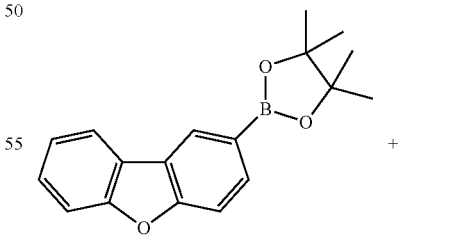

+

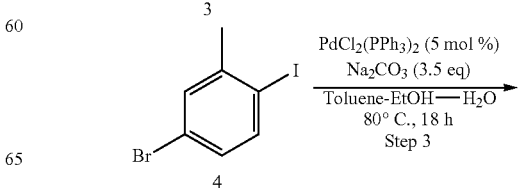

-continued

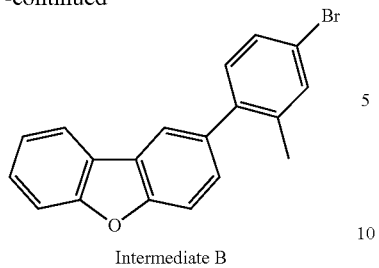

Intermediate B

| Reagent | Quantity (g) | Vol. (mL) | MW | Moles | Eq. |
|---|---|---|---|---|---|
| Intermediate 3 | 128 | | 294.6 | 0.435 | 1 |
| Intermediate 4 | 128.8 | | 296.13 | 0.435 | 1 |
| Sodium carbonate | 161.3 | | 105.98 | 1.522 | 3.5 |
| PdCl$_2$(PPh$_3$)$_2$ | 15.2 | | 701.90 | 0.021 | 0.05 |
| Toluene:EtOH:water (1:1:0.5) | | 2500 | | | |

Apparatus Set-Up:

A 5 L 3-necked round-bottomed flask, equipped with a mechanical overhead stirrer, reflux condenser, nitrogen inlet and exhaust.

Experimental Procedure:

Intermediate 3 (128 g, 0.435 mol) and intermediate 4 (128.8 g, 0.435 mol) were taken in toluene (1 L) and ethanol (1 L).

Sodium carbonate solution (161.3 g, 1.522 mol, dissolved in 500 mL of water) was added.

The reaction mixture was degassed with nitrogen for an hour.

PdCl$_2$ (PPh$_3$)$_2$ (15.2 g, 0.021 mol) was added and heated at 80° C. for 18 h.

After completion of the reaction, the mixture was filtered through a Florosil-silica plug and concentrated.

The residue was dissolved in ethyl acetate (2 L), washed with water (1 L), brine (1 L), dried over sodium sulphate and concentrated.

The crude product (159 g) was purified by silica column chromatography using 5 to 6% ethyl acetate in hexane as an eluent to get 65 g of Intermediate B with 81% HPLC purity.

It was again purified by reverse phase column chromatography (in 5 g per run) using water/acetonitrile as an eluent to get 35.6 g of Intermediate B.

The material was dissolved in dichloromethane (500 mL), heated to 45° C., filtered the hot solution and concentrated to get 35 g of Intermediate B with 99.64% HPLC purity as viscous oil.

$^1$H-NMR (400 MHz, CDCl$_3$): δ [ppm] 2.29 (s, 3H), 7.19 (d, J=8.0 Hz, 1H), 7.37-7.42 (m, 3H), 7.47-7.52 (m, 2H), 7.61 (d, J=8.4 Hz, 2H), 7.86 (s, 1H), 7.96 (d, J=7.6 Hz, 1H).

Intermediate C

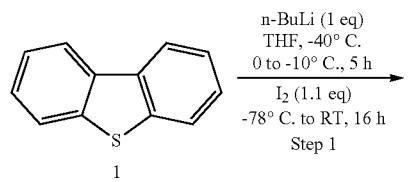

-continued

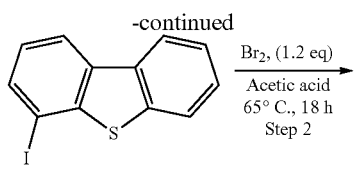

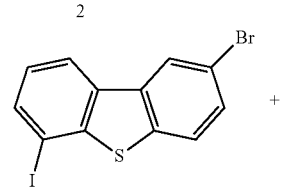

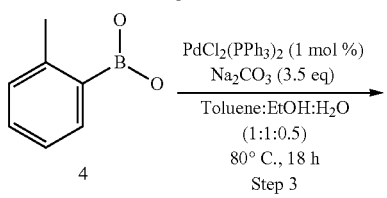

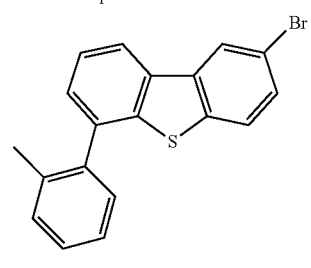

Intermediate C

Step 1—Synthesis of Intermediate 2

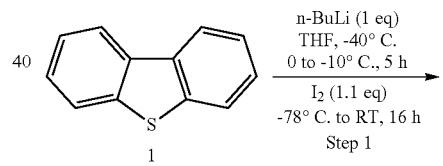

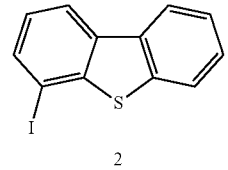

| S. No | Reagent | Quantity (g) | Vol. (mL) | MW | Moles | Eq |
|---|---|---|---|---|---|---|
| 1 | Dibenzothiophene | 300 | | 184.26 | 1.628 | 1 |
| 2 | 2.5M n-BuLi in hexane | | 651 | | 1.628 | 1 |
| 3 | Tetrahydrofuran | | 5000 | | | |
| 4 | Iodine | 454 | | 253.9 | 1.7908 | 1.1 |

Apparatus Set-Up:

A 10 L 3-necked round-bottomed flask, equipped with a mechanical overhead stirrer, nitrogen inlet and exhaust.

Experimental Procedure:

Dibenzothiophene (300 g, 1.628 mol) was taken in dry tetrahydrofuran (5 L).

The reaction mixture was cooled to −40° C. using dry ice/acetonitrile bath.

n-BuLi (651 mL, 2.5 M in hexane) was added drop wise slowly.

The reaction mixture was stirred at 0° C. to −10° C. for 5 hours, then cooled to −78° C. and iodine (454 g, 1.7908 mol) was added portion wise slowly.

The reaction mixture was slowly allowed to room temperature and stirred for 16 hours.

The reaction mixture was quenched with water (500 mL) and extracted with ethyl acetate (2×1 L).

The combined organic phase was washed with sodium thiosulphate solution (2 L), water (1 L), brine (1 L), dried over sodium sulphate and concentrated (370 g).

The crude product was purified by hot acetonitrile crystallization to get 300 g of intermediate 2 with 98.75% HPLC purity.

$^1$H-NMR (400 MHz, CDCl$_3$): δ [ppm] δ 7.20-7.24 (m, 1H), 7.49-7.55 (m, 2H), 7.84 (dd, J=0.8 Hz, 7.6 Hz, 1H), 7.89-7.93 (m, 1H), 8.10-8.14 (m, 1H), 8.18 (dd, J=0.8 Hz, 8.0 Hz, 1H).

Step 2—Synthesis of Intermediate 3

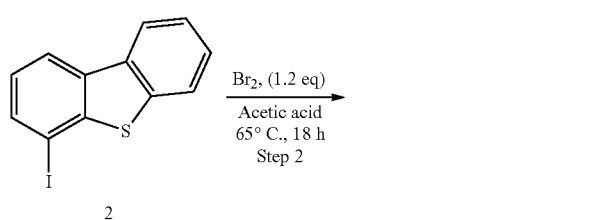

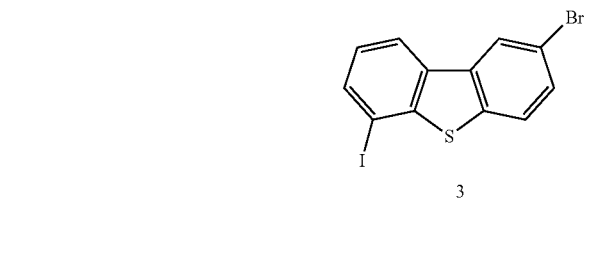

| Reagent | Quantity (g) | Vol. (mL) | MW | Moles | Eq. |
|---|---|---|---|---|---|
| Intermediate 2 | 300 | | 310.15 | 0.9672 | 1 |
| Bromine | 185 | 59.8 | 159.81 | 1.1607 | 1.2 |
| CH$_3$COOH | | 1800 | | | 6v |

Apparatus Set-Up:

A 5 L 3-necked round-bottomed flask, equipped with a mechanical overhead stirrer, reflux condenser, nitrogen inlet and exhaust.

Experimental Procedure:

Intermediate 2 (300 g, 0.9672 mol) was taken in acetic acid (1.8 L).

Bromine (185 g, 59.8 mL, 1.1607 mol) was added slowly drop wise.

Then the reaction mixture was heated at 65° C. for 18 h.

The reaction mixture was filtered, washed with sodium thiosulfate solution (2 L), water (1 L) and dried under vacuum to get 240 g of crude product.

The crude product was recrystallized twice with hot toluene and filtered to get 150 g of intermediate 3 with 97.01% HPLC purity.

$^1$H-NMR (400 MHz, CDCl$_3$): δ [ppm] 7.21-7.25 (m, 1H), 7.60 (dd, J=2.0 Hz, 8.6 Hz, 1H), 7.75 (d, J=8.40 Hz, 1H), 7.86 (d, J=6.8 Hz, 1H), 8.12 (dd, J=0.8, 8.0 Hz, 1H), 8.22 (s, 1H).

Step 3—Synthesis of Intermediate C

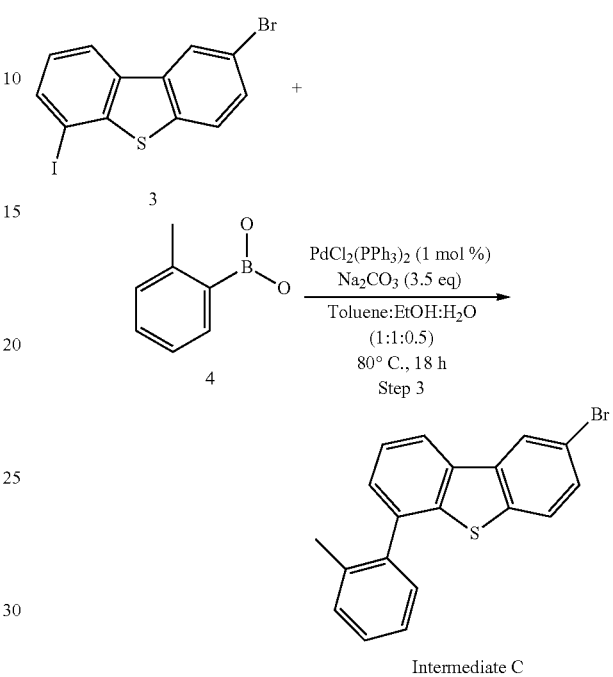

| Reagent | Quantity (g) | Vol. (mL) | MW | Moles | Eq. |
|---|---|---|---|---|---|
| Intermediate 3 | 150 | | 389.05 | 0.3855 | 1 |
| Intermediate 4 | 52.4 | | 135.95 | 0.3855 | 1 |
| Na$_2$CO$_3$ | 143 | | 105.98 | 1.3492 | 3.5 |
| PdCl$_2$(PPh$_3$)$_2$ | 2.7 | | 701.90 | 0.0039 | 0.01 |
| Toluene:EtOH:water (2:2:1) | | 3750 | | | |

Apparatus Set-Up:

A 10 L 3-necked round-bottomed flask, equipped with a mechanical overhead stirrer, reflux condenser, nitrogen inlet and exhaust.

Experimental Procedure:

Intermediate 3 (150 g, 0.3855 mol), 2-methyl phenyl boronic acid (52.4 g, 0.3855 mol) were taken in toluene (1500 mL) and ethanol (1500 mL) mixture.

Sodium carbonate solution (143 g, 1.3492 mol dissolved in 750 mL of water) was added.

The mixture was degassed with nitrogen for an hour.

PdCl$_2$(PPh$_3$)$_2$ (2.7 g, 0.0039 mol) was added and heated to 80° C. for 18 h. The reaction mixture was filtered through a fluorosil plug and concentrated.

The residue was dissolved in ethyl acetate (2 L), washed with water (1 L), brine (1 L), dried over sodium sulphate and concentrated to get 180 g of crude product.

The crude product thus obtained was purified by silica column chromatography using hexane as an eluent to get 138 g of Intermediate C with 80% HPLC purity.

The product was again passed through a silica column using hexane as an eluent to get the following fractions:

Fraction 1: 50 g of Intermediate C with 96% HPLC purity

Fraction 2: 48 g of Intermediate C with 89% HPLC purity

Fraction 3: 30 g with 60% HPLC purity 50 g of Intermediate C with 96% HPLC purity was refluxed with acetonitrile and cooled to −30° C. and filtered to get 30 g of Intermediate C with 98.4% HPLC purity as white solid.

30 g of Intermediate C with 98.4% HPLC purity was again refluxed with acetonitrile and cooled to room temperature to get 28 g of Intermediate C with 99.53% HPLC purity.

48 g of Intermediate C was again purified by silica column chromatography using hexane as an eluent to get 39 g of Intermediate C with 96% HPLC purity which was again recrystallized from hot acetonitrile twice to get 24 g of Intermediate C with 99.11% HPLC purity.

28 g of Intermediate C with 99.53% HPLC purity and 24 g of Intermediate C with 99.11% HPLC purity were combined and hot filtration was done with dichloromethane at 45° C. to get 52 g of Intermediate C with 99.26% HPLC purity.

All low pure fractions were combined and purified by silica column chromatography using only hexane for long run and repeated recrystallization with hot acetonitrile to get 31.28 g of Intermediate C with 99.13% HPLC purity.

$^1$H-NMR (400 MHz, CDCl$_3$): δ [ppm] 2.20 (s, 3H), 7.33-7.41 (m, 5H), 7.54-7.60 (m, 2H), 7.66 (d, J=8.48 Hz, 1H), 8.13 (d, J=7.92 Hz, 1H), 8.27 (s, 1H).

Intermediate D

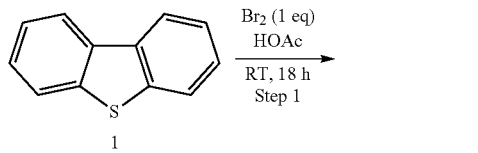

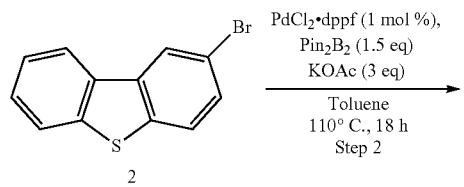

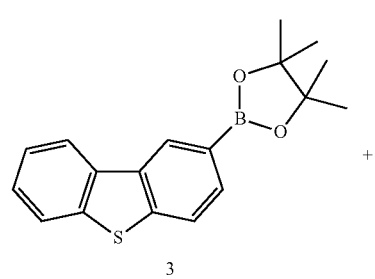

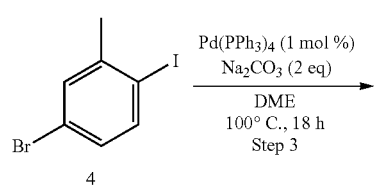

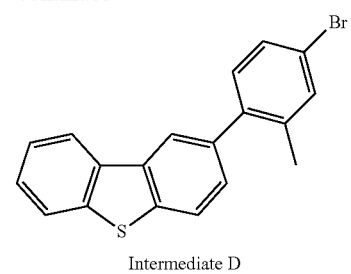

Intermediate D

Step 1—Synthesis of Intermediate 2

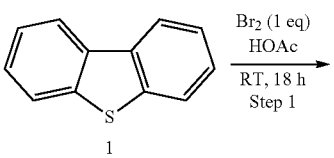

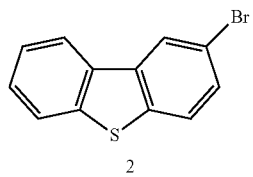

| S. No | Reagent | Quantity (g) | Vol. (mL) | MW | Moles | Eq |
|---|---|---|---|---|---|---|
| 1 | Dibenzothiophene | 300 | | 184.26 | 1.628 | 1 |
| 2 | Bromine | 260.17 | 83.9 | 159.8 | 1.628 | 1 |
| 3 | Acetic acid | | 3000 | | | |

Apparatus Set-Up:

A 5 L 3-necked round-bottomed flask, equipped with a mechanical overhead stirrer, reflux condenser, nitrogen inlet and exhaust.

Experimental Procedure:

Dibenzothiophene (300 g, 1.628 mol) was taken in acetic acid (3 L) and warmed to 45° C. to obtain a clear solution.

After getting a clear solution, the reaction mixture was allowed to warm to room temperature and bromine (83.9 mL, 1.628 mol) was slowly added.

The reaction mixture was stirred at room temperature for 18 h.

The reaction mixture was filtered, washed with water (1 L) and dried.

The solid obtained was dissolved in ethyl acetate (4 L), washed with sodium thiosulphate solution (1 Kg in 3 L of water), water (1 L), dried over sodium sulphate and concentrated to get 245 g of crude product.

The crude product (245 g) was purified by hot toluene/acetonitrile crystallization to get 210 g of intermediate 2 containing ~5% of dibromide impurity.

$^1$H-NMR (400 MHz, CDCl$_3$): δ [ppm] 7.46-7.52 (m, 2H), 7.54-7.59 (m, 1H), 7.71 (d, J=8.40 Hz, 1H), 7.84-7.88 (m, 1H), 8.08-8.12 (m, 1H), 8.28 (s, 1H).

Step 2—Synthesis of Intermediate 3

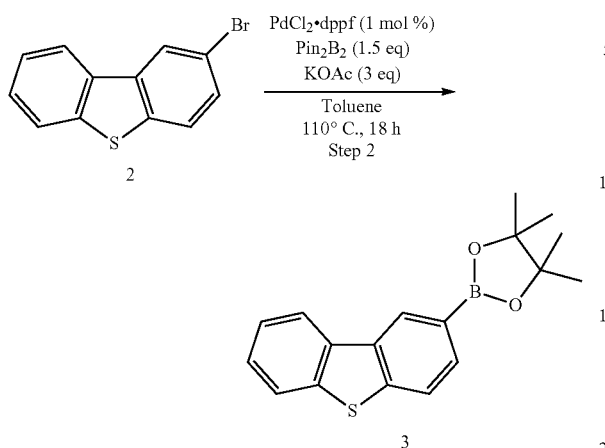

| S. No. | Reagent | Quantity (g) | Vol. (mL) | MW | Moles | Eq. |
|---|---|---|---|---|---|---|
| 1 | Intermediate 2 | 210 | | 263.16 | 0.797 | 1 |
| 2 | Bis(pinacolato)diboron | 303.9 | | 253.9 | 1.196 | 1.5 |
| 3 | Potassium acetate | 234.67 | | 98.15 | 2.39 | 3.0 |
| 4 | PdCl$_2$•dppf | 6.5 | | 816 | 0.0079 | 0.01 |
| 5 | Toluene | | 2200 | | | |

Apparatus Set-Up:

A 10 L 3-necked round-bottomed flask, equipped with a mechanical overhead stirrer, nitrogen inlet and exhaust.

Experimental Procedure:

Intermediate 2 (210 g, 0.797 mol) was taken in toluene (2.2 L).

Bis (pinacolato)diboron (303.9 g, 1.196 mol) and potassium acetate (234.67 g, 2.39 mol) were added.

The reaction mixture was degassed with nitrogen for an hour.

PdCl$_2$.dppf (6.5 g, 0.0079 mol) was added and heated at 110° C. for 18 h.

After completion of the reaction, it was filtered through a Florosil-silica plug and concentrated.

The residue was dissolved in ethyl acetate (2 L), washed with water (1 L), brine (1 L), dried over sodium sulphate and concentrated.

The crude product (280 g) was triturated with hexane and filtered to get 200 g of Intermediate 3.

$^1$H-NMR (400 MHz, CDCl$_3$): δ [ppm] 1.43 (s, 12H), 7.47-7.49 (m, 2H), 7.86-7.92 (m, 3H), 8.26-8.29 (m, 1H), 8.65 (s, 1H).

Step 3—Synthesis of Intermediate D

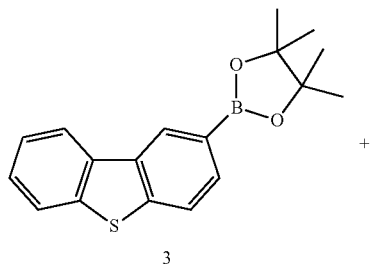

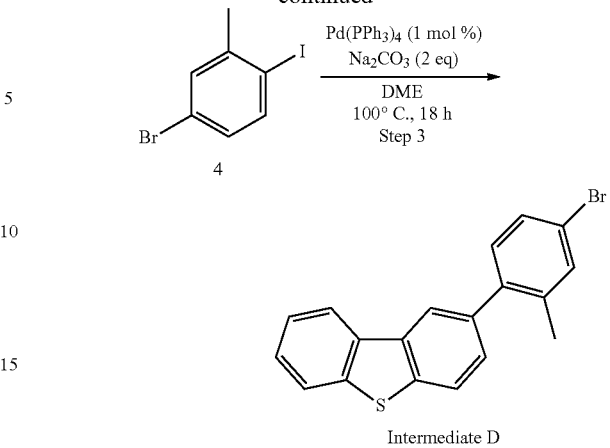

| Reagent | Quantity (g) | Vol. (mL) | MW | Moles | Eq. |
|---|---|---|---|---|---|
| Intermediate 3 | 200 | | 310.23 | 0.644 | 1 |
| Intermediate 4 | 190.9 | | 296.13 | 0.644 | 1 |
| Sodium carbonate | 136.5 | | 105.98 | 1.288 | 2 |
| Pd(PPh$_3$)$_4$ | 7.44 | | 1155.5 | 0.0064 | 0.01 |
| DME | | 2000 | | | |
| Water | | 1000 | | | |

Apparatus Set-Up:

A 10 L 3-necked round-bottomed flask, equipped with a mechanical overhead stirrer, reflux condenser, nitrogen inlet and exhaust.

Experimental Procedure:

Intermediate 3 (200 g, 0.644 mol) and intermediate 4 (190.9 g, 0.644 mol) were taken in 1, 2-dimethoxy ethane (2 L).

Sodium carbonate solution (136.5 g, 1.288 mol, dissolved in 1 L of water) was added.

The reaction mixture was degassed with nitrogen for an hour.

Pd(PPh$_3$)$_4$ (7.44 g, 0.00644 mol) was added and heated at 100° C. for 18 h.

After completion of the reaction, it was filtered through a Florosil-silica plug and concentrated.

The residue was dissolved in ethyl acetate (2 L), washed with water (1 L), brine (1 L), dried over sodium sulphate and concentrated.

The crude product (200 g) was purified by silica column chromatography using hexane as an eluent to get 160 g of Intermediate D with 93% HPLC purity.

It was again purified by hot acetonitrile crystallization to get 135 g of Intermediate D with 97% HPLC purity.

It was further purified by hot acetonitrile crystallization to get 130 g of Intermediate D with 98.22% HPLC purity.

130 g of Intermediate D at 98.22% HPLC purity was crystallized with hot ethyl acetate/methanol (1:1.5) to get 100 g of Intermediate D with 98.9% HPLC purity.

100 g of Intermediate D at 98.9% HPLC purity was crystallized with hot ethyl acetate/methanol (1:1) to get 60 g of Intermediate D with 99.79% HPLC purity.

Filtrate obtained from all the above crystallizations were combined and concentrated to get 55 g at 97.2% HPLC purity.

55 g of Intermediate D 97.2% HPLC purity was crystallized with hot ethyl acetate/methanol (1:0.8) to get 24 g of Intermediate D with 99.81% HPLC purity.

24 g of Intermediate D at 99.81% purity and 60 g of 99.79% purity were combined, dissolved in dichloromethane (500 mL), heated to 45° C., filtered the hot solution and concentrated to get 80.5 g of Intermediate D with 99.70% HPLC purity as white solid.

$^1$H-NMR (400 MHz, CDCl$_3$): δ [ppm] 2.31 (s, 3H), 7.21 (d, J=8.00 Hz, 1H), 7.40-7.45 (m, 2H), 7.48-7.52 (m, 3H), 7.89-7.91 (m, 2H), 8.07 (s, 1H), 8.15-8.17 (m, 1H).

Compound Example A

Compound Example A was prepared according to the following reaction scheme:

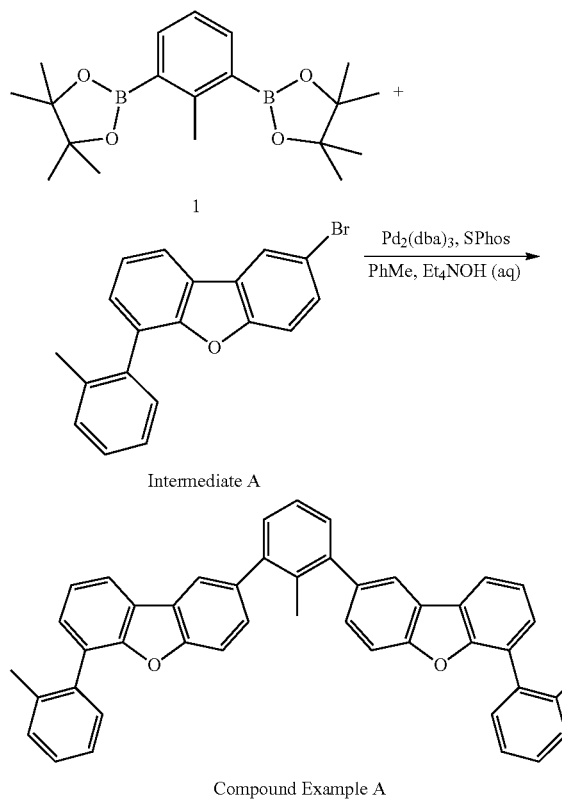

Intermediate A

Compound Example A

Compound 1 is commercially available, or can be synthesised as shown in WO2012/073902.

A stirred mixture of compound 1, Intermediate A (2.1 eq), and toluene (10 wt % solution) was degassed for 45 min. Tris(dibenzylideneacetone)dipalladium(0) (0.003 eq) and SPhos (0.006 eq) were added to the stirred mixture which was degassed for a further 15 min. The resulting stirred mixture was heated and a degassed (1 h) solution of tetraethylammonium hydroxide (20 wt %, 4 eq) was added dropwise. The resulting stirred mixture was heated under reflux overnight, then cooled to room temperature, separated, washed with water (×5) and concentrated in vacuo. The crude product was then purified by column chromatography (heptane, with increasing volume fractions of DCM) and several recrystallisations (from mixtures of toluene-methanol and/or toluene-heptane and/or n-butylacetate-toluene as appropriate) until the desired purity was reached. The resulting white solid was then sublimed to yield the desired product as a colourless solid or glass.

Yield: 2.05 g, 46%; Purity: 99.8% (HPLC); $^1$H NMR (600 MHz, THF) δ=8.08 (2H, d, J=1.6 Hz), 8.05-8.05 (1H, m), 8.06 (1H, dd, J=7.6 Hz, J=1.2 Hz), 7.60 (2H, d, J=8.4 Hz), 7.48 (2H, dd, J=8.5 Hz, J=1.8 Hz), 7.42-7.46 (2H, m), 7.37 (2H, dd, J=7.3 Hz, J=1.2 Hz), 7.34-7.36 (2H, m), 7.33-7.36 (3H, m), 7.33-7.34 (2H, m), 7.34 (1H, s), 7.31-7.34 (2H, m), 7.26-7.30 (2H, m), 2.23 (6H, s), 2.20 (3H, s)

Compound Examples B-D

Compound Examples B-D were prepared as described for Compound Example A except that Intermediates B-D respectively were used in place of Intermediate A.

Compound Example B:

Yield: 2.93 g, 66%; Purity: 99.7% (HPLC); $^1$H NMR (600 MHz, THF) δ=8.07 (2H, d, J=1.5 Hz), 8.05 (2H, ddd, J=7.5 Hz, J=1.1 Hz, J=0.6 Hz), 7.66 (2H, d, J=8.4 Hz), 7.61 (2H, dt, J=8.2 Hz, J=0.6 Hz), 7.51 (2H, dd, J=8.4 Hz, J=1.9 Hz), 7.48 (2H, ddd, J=8.3 Hz, J=7.2 Hz, J=1.2 Hz), 7.38 (2H, d, J=7.7 Hz), 7.36 (2H, dd, J=7.6 Hz, J=0.8 Hz), 7.35 (2H, s), 7.30-7.33 (11H, m), 7.26-7.30 (4H, m), 2.38 (6H, s), 2.27 (3H, s)

Compound Example C

Yield: 4.62 g, 71%; Purity: 99.9% (HPLC); $^1$H NMR (600 MHz, THF) δ=8.31 (2H, s), 8.29 (2H, d, J=7.8 Hz), 7.90 (2H, d, J=8.1 Hz), 7.56 (2H, t, J=7.6 Hz), 7.50 (2H, d, J=8.0 Hz), 7.36 (3H, br s), 7.34-7.34 (1H, m), 7.32-7.37 (6H, m), 7.32-7.35 (2H, m), 7.27-7.31 (2H, m), 2.23 (3H, s), 2.18 (6H, s)

Compound Example D

Yield: 0.85 g, 20%, Purity: 99.92% (HPLC); $^1$H NMR (600 MHz, THF) δ=8.29-8.32 (4H, m), 7.97 (2H, d, J=8.2 Hz), 7.90-7.94 (2H, m), 7.53 (2H, dd, J=8.1 Hz), 7.44-7.49 (4H, m), 7.41 (2H, d, J=7.7 Hz), 7.36 (2H, s), 7.30-7.34 (3H, m), 7.27-7.29 (2H, m), 2.40 (6H, s), 2.28 (3H, s)

Compound Example E

Compound Example E was prepared according to the following reaction scheme:

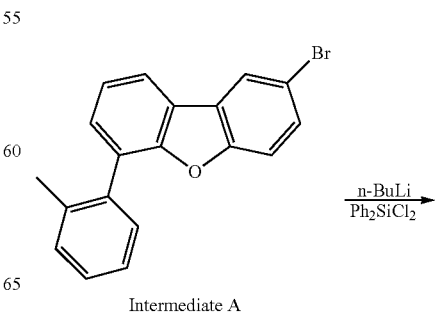

Intermediate A

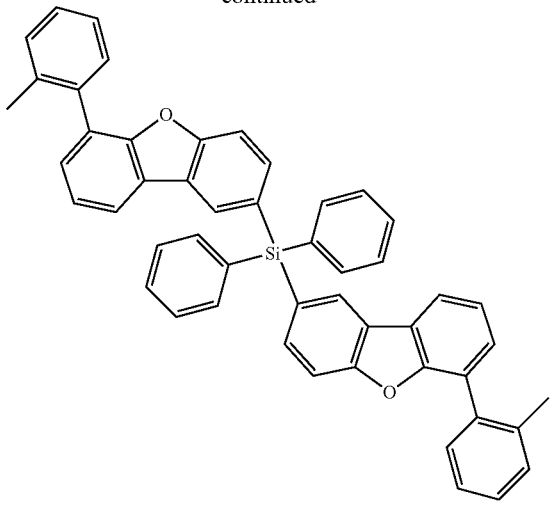

A solution of Intermediate A in anhydrous THF (approx. 10 wt %) was cooled to −78° C. and stirred under a nitrogen atmosphere. n-Butyllithium (2.5M in hexanes; 1.05 eq) was added dropwise to the solution, maintaining internal reaction temperature below −75° C. The reaction was stirred for 1-2 hr at −78° C. Diphenyldichlorosilane (0.45 eq) was added dropwise to the reaction and the mixture was stirred for 4-5 hours at −78° C., before allowing to warm slowly to room temperature while stirring overnight. The reaction was then quenched by addition of water, and the solvents were removed in vacou, leaving a gummy white solid. The crude material was purified by column chromatography on silica, eluting with a mixture of dichloromethane and heptane, followed by repeated crystallisations from a mixture of Toluene and Methanol. Finally, the material was sublimed, giving a colourless solid or glass.

Yield 0.58 g, 31%; Purity: 99.93% (HPLC); $^1$H NMR (600 MHz, THF) δ=8.37 (2H, s), 7.97 (2H, dd, J=7.3 Hz, J=1.6 Hz), 7.66-7.70 (4H, m), 7.69 (2H, ddd, J=8.1 Hz, J=4.9 Hz, J=1.3 Hz), 7.59 (2H, d, J=8.3 Hz), 7.45 (2H, ddt, J=7.9 Hz, J=6.5 Hz, J=1.4 Hz), 7.41 (4H, tt, J=7.5 Hz, J=1.4 Hz), 7.37 (2H, t, J=7.5 Hz), 7.33-7.36 (1H, m), 7.31-7.36 (2H, m), 7.31-7.35 (3H, m), 7.29-7.33 (2H, m), 7.27 (2H, td, J=7.2 Hz, J=1.6 Hz), 2.22 (6H, s)

Compound Examples F-H

Compound Examples F-H were prepared as described for Compound Example E except that Intermediates B-D respectively were used in place of Intermediate A.

Compound Example F

Yield 0.30 g, 12%; Purity: 99.96% (HPLC); $^1$H NMR (600 MHz, CDCl$_3$): δ=7.93-7.98 (2H, m), 7.92-7.97 (2H, m), 7.70 (4H, dd, J=8.0 Hz, J=1.4 Hz), 7.60-7.63 (2H, m), 7.58-7.61 (2H, m), 7.57 (2H, s), 7.54 (2H, d, J=7.5 Hz), 7.45-7.50 (4H, m), 7.45-7.47 (2H, m), 7.42-7.46 (4H, m), 7.34-7.38 (4H, m), 2.32 (6H, s)

Compound Example G

Yield 0.72 g, 16%; Purity: 99.83% (HPLC); $^1$H NMR (600 MHz, THF) δ=8.26-8.29 (2H, m), 8.27 (2H, s), 7.95 (2H, d, J=8.2 Hz), 7.91 (2H, d, J=7.0 Hz), 7.66-7.69 (4H, m), 7.61 (2H, s), 7.54 (2H, d, J=7.5 Hz), 7.50 (2H, dd, J=8.2 Hz, J=1.6 Hz), 7.44-7.47 (2H, m), 7.43-7.45 (2H, m), 7.43-7.48 (2H, m), 7.40-7.44 (4H, m), 7.38 (2H, d, J=7.4 Hz), 2.32 (6H, s)

Compound Example H

Yield 0.35 g, 10%; Purity: 99.92% (HPLC); $^1$H NMR (600 MHz, THF) δ=8.29-8.32 (4H, m), 7.97 (2H, d, J=8.2 Hz), 7.90-7.94 (2H, m), 7.53 (2H, dd, J=8.1 Hz, J=1.6 Hz), 7.44-7.49 (4H, m), 7.41 (2H, d, J=7.7 Hz), 7.36 (2H, s), 7.30-7.34 (3H, m), 7.27-7.29 (2H, m), 2.40 (6H, s), 2.28 (3H, s)

Compound Example J-M 3,3'-Dimethyl-4,4'-bis(trifluoromethanesulfonyloxy)tetraphenylmethane was prepared according to the following reaction scheme:

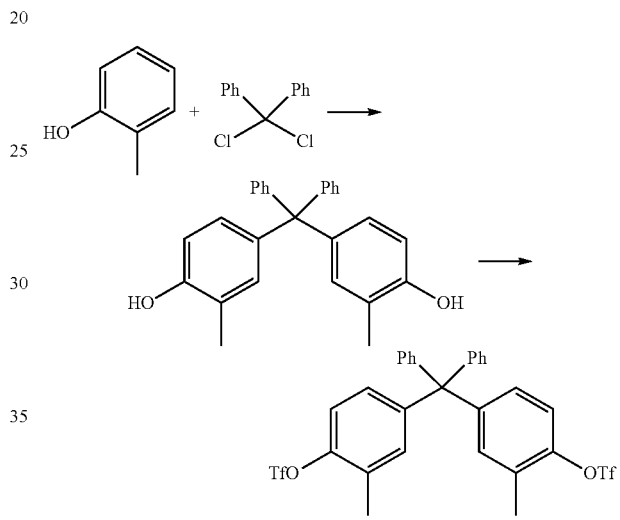

Dichlorodiphenylmethane (1.60 mL, 8.43 mmol) was added dropwise to o-cresol (2.28 g, 21.1 mmol) under a N$_2$ atmosphere. The resulting red reaction mixture was stirred at room temperature for 18 h. GCMS analysis of an aliquot of the reaction mixture revealed that no product had been formed and the reaction mixture was therefore heated at 50° C. for 30 hours before being allowed to cool to room temperature. The reaction mixture was dissolved in the minimum amount of EtOAc (~10 mL) and then further diluted with heptane (20 mL). The resulting solution was wet loaded onto a column containing 340 g silica. Purification by column chromatography (gradient elution, 0-50% EtOAc in heptane) gave 3,3'-Dimethyl-4,4'-dihydroxytetraphenylmethane as a white solid that slowly turned yellow on standing (806 mg, 25%, 99.27% HPLC purity); δ$_H$ (600 MHz, CDCl$_3$): 2.14 (6H, s, C(3)Me, C(3')Me), 4.52 (2H, s, C(4)OH, C(4')OH), 6.64 (2H, d, J=8.6 Hz, C(5)H, C(5')H), 6.82 (2H, dd, J=8.6, 2.4 Hz, C(6)H, C(6')H), 6.93 (2H, d, J=2.4 Hz, C(2)H, C(2')H), 7.14-7.20 (6H, m, Ph), 7.21-7.25 (4H, m, Ph); m/z (ESI$^-$) 379 ([M-H]$^-$).

Triflic anhydride (0.85 mL, 5.04 mmol) was added dropwise to 3,3'-dimethyl-4,4'-dihydroxytetraphenylmethane (800 mg, 2.11 mmol) and pyridine (0.96 mL, 6.31 mmol) in CH$_2$Cl$_2$ (10 mL) under a N$_2$ atmosphere at 0° C. The reaction mixture was allowed to warm to room temperature and stirred for 16 h before being filtered through a silica plug (eluent 10% EtOAc in heptane). The filtrate was concentrated in vacuo and then wet loaded onto a column containing 100 g silica. Purification by column chromatography (gradient elution, 0-10% EtOAc in heptane) gave 3,3'-dimethyl-4,4'-bis(trifluoromethanesulfonyloxy)tetraphenylmethane as a white solid (476 mg, 30%); δ$_H$(600 MHz, CDCl$_3$): 2.29 (6H, s, C(3)Me, C(3')Me), 7.06 (2H, dd, J=9.0, 2.6 Hz, C(6)H, C(6')H), 7.10-7.15 (8H, C(2)H, C(2')H, C(5)H, C(5')H, Ph), 7.21-7.30 (6H, m, Ph); m/z (ESI$^-$) 643 ([M-H]$^-$).

Compound examples J-M may be prepared from 3,3'-Dimethyl-4,4'-bis(trifluoromethanesulfonyloxy)tetraphenylmethane according to the following reaction scheme:

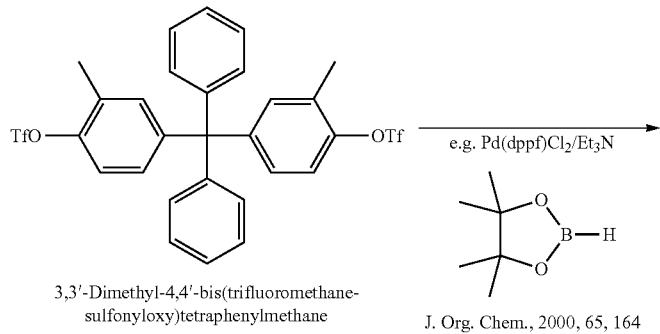

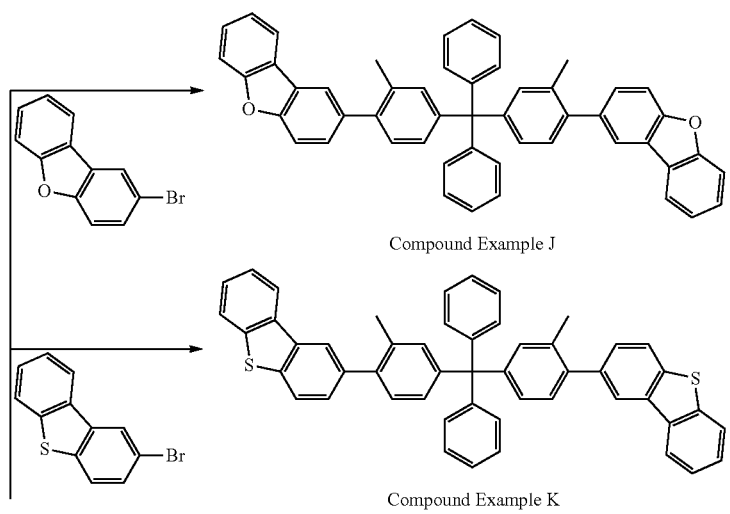

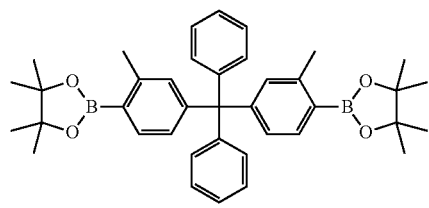

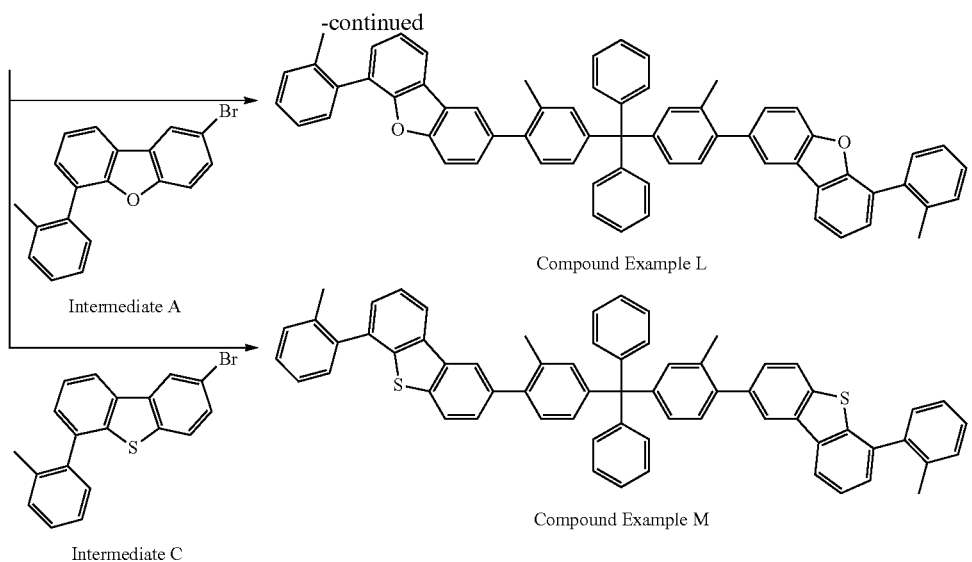
Compound Example N
Compound Example N may be prepared according to the following reaction scheme:
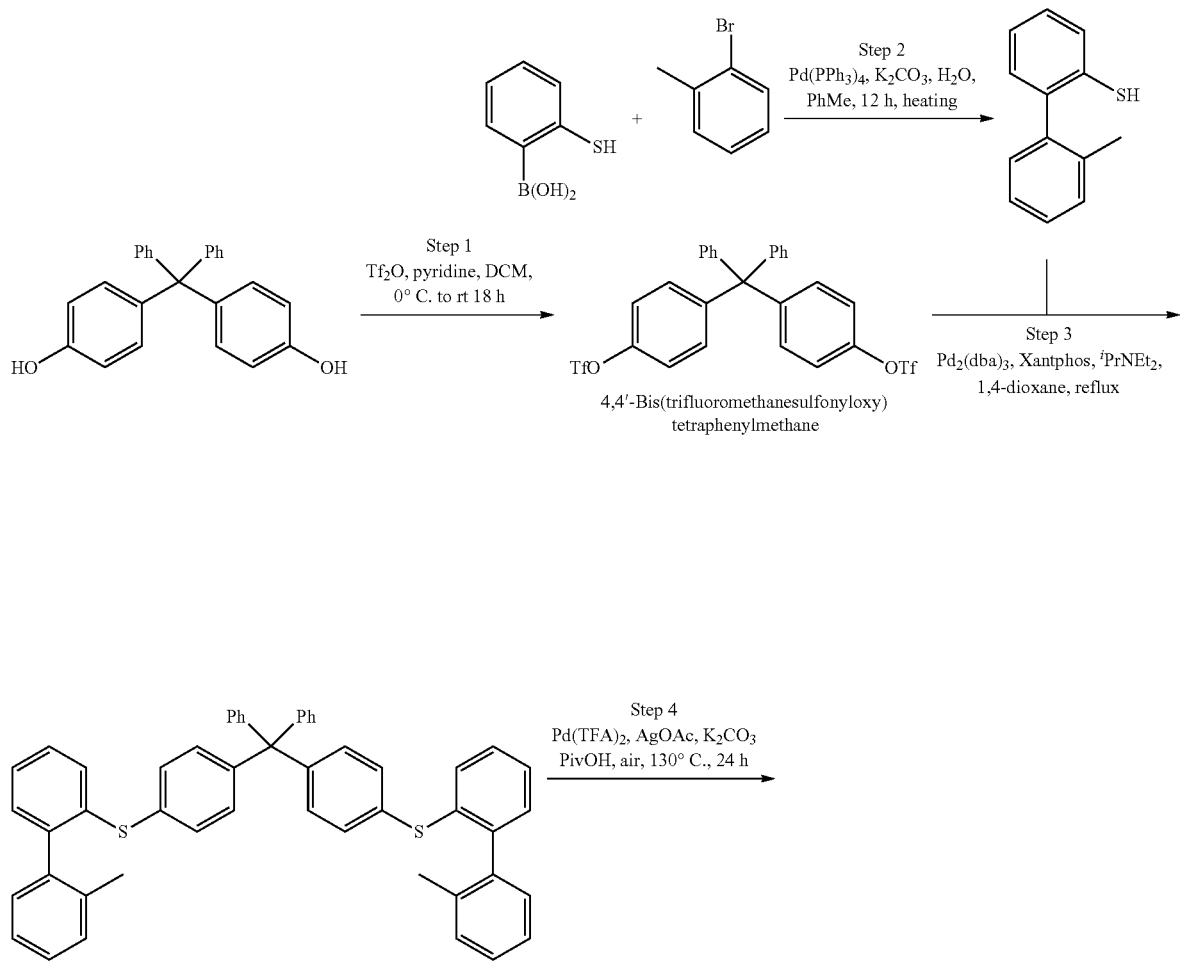

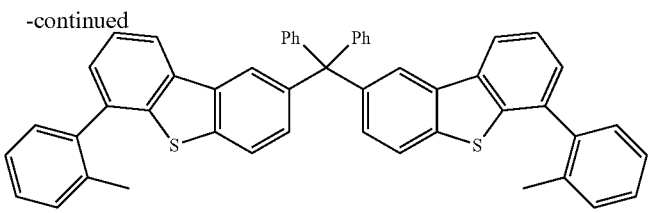

Compound Example N

Step 1 - as per 3,3′-Dimethyl-4,4′-bis(trifluoromethanesulfonyloxy)tetraphenylmethane
Step 2 - US20150041770
Step 3 - Org. Lett., 2004, 6, 4587
Step 4 - Chem. Eur. J., 2014, 20, 7258

Compound Example O

Compound Example O may be prepared according to the following reaction scheme:

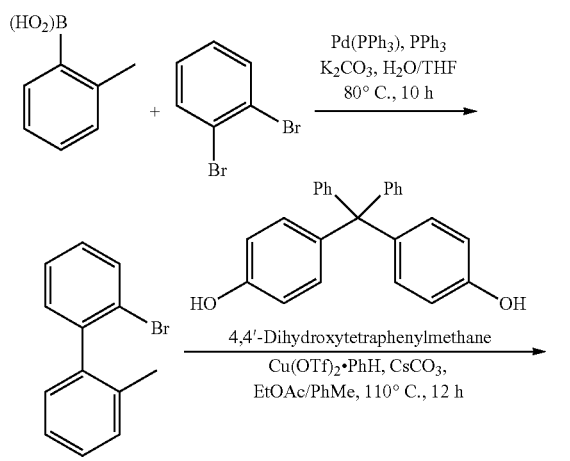

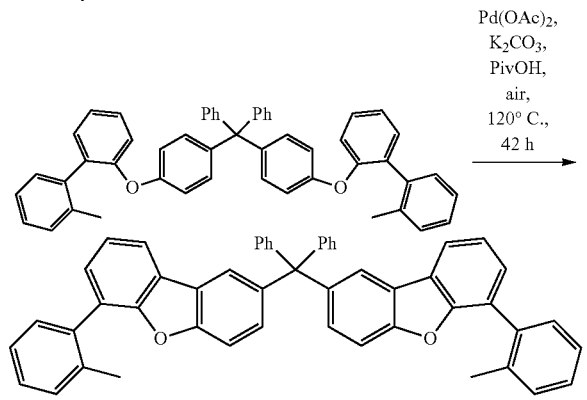

Compound Example O

Step 1 - Synlett, 2009, 7, 1081
Step 2 - J. Am. Chem. Soc., 1997, 119, 10539
Step 3 - J. Org. Chem., 2008, 73, 5022

Material Evaluation

The photoluminescent quantum yield (PLQY) of a composition of a host material with a a blue phosphorescent tris(phenyltriazole) iridium (III) compound was measured.

Films were spun on quartz disks and measurements were performed under nitrogen in an integrating sphere connected to Hamamatsu C9920-02 with Mercury lamp E7536 and a monochromator for choice of exact wavelength.

TABLE 1

| Host | PLQY (%) |
| --- | --- |
| Comparative Compound 1 | 73 |
| Compound Example A | 84 |
| Compound Example B | 80 |

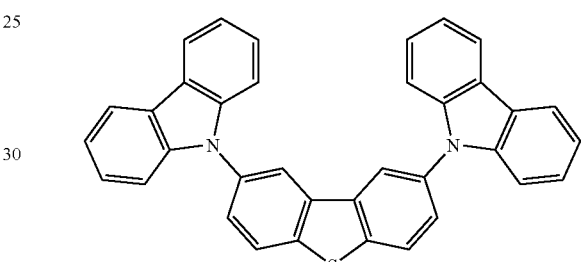

Comparative Compound 1

Compound Examples A and B both have a HOMO level in the range of 5.9-6.1 as measured by square wave voltammetry whereas Comparative Compound 1 has a HOMO level of 5.7 eV.

HOMO and LUMO values were measured by square wave voltammetry.

Apparatus for HOMO or LUMO energy level measurements by SWV comprise a CHI 660D Potentiostat; a 3 mm diameter glassy carbon working electrode; a leak free Ag/AgCl reference electrode; Pt wire counter electrode; and a cell containing 0.1M tetrabutylammonium hexafluorophosphate in acetonitrile:toluene (1:1).

A cell containing 0.1M tetrabutylammonium hexafluorophosphate in acetonitrile:toluene (1:1) was used and Ferrocene is added to a fresh cell of identical solvent composition for calculation purposes where the potentials are determined for the oxidation and reduction of ferrocene versus Ag/AgCl using cyclic voltammetry (CV). The sample was dissolved in Toluene (3 mg/ml) and added directly to the cell LUMO=4.8−$E$ ferrocene (peak to peak average)−$E$ reduction of sample (peak maximum)

HOMO=4.8−$E$ ferrocene (peak to peak average)+$E$ oxidation of sample (peak maximum)

The SWV experiment was run at 15 Hz frequency; 25 mV amplitude and 0.004V increment steps under an Argon gas purge.

White Device Example 1

A white organic light-emitting device having the following structure was prepared:

ITO/HIL/LEL(R)/LEL(G,B)/HBL/ETL/Cathode wherein ITO is an indium-tin oxide anode; HIL is a hole-injecting layer comprising a hole-injecting material, LEL (R) is a red light-emitting hole-transporting layer, LEL (G, B) is a green and blue light-emitting layer, HBL is a hole-blocking layer; and ETL is an electron-transporting layer.

A substrate carrying ITO (45 nm) was cleaned using UV/Ozone. A hole injection layer was formed to a thickness of about 35 nm by spin-coating a formulation of a hole-injection material available from Nissan Chemical Industries. A red light-emitting layer was formed to a thickness of about 20 nm by spin-coating a polymer comprising amine repeat units of formula (VII), crosslinkable repeat units and Red Phosphorescent Repeat Unit 1, and crosslinking the polymer by heating at 180° C. The green and blue light-emitting layer was formed to a thickness of about 70 nm by spin-coating Compound Example A (74 wt %), Green Phosphorescent Emitter 1 (1 wt %) and Blue Phosphorescent Emitter 2, illustrated below (24 wt %). A hole-blocking layer of Hole Blocking Compound 1 was deposited over the light-emitting layer to a thickness of 10 nm. An electron-transporting layer was formed by spin-coating a polymer comprising the cesium salt of Electron-Transporting Unit 1 as described in WO 2012/133229 to a thickness of 10 nm. A cathode was formed on the electron-transporting layer of a first layer of sodium fluoride of about 3.5 nm thickness, a layer of aluminium of about 100 nm thickness and a layer of silver of about 100 nm thickness.

Red Phosphorescent Repeat Unit 1

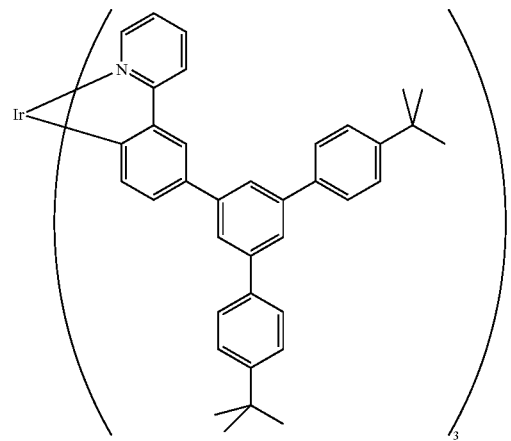

Green Phosphorescent Emitter 1

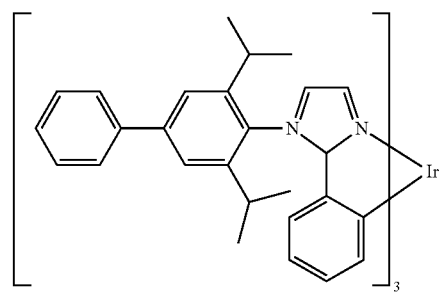

Blue Phosphorescent Emitter 2

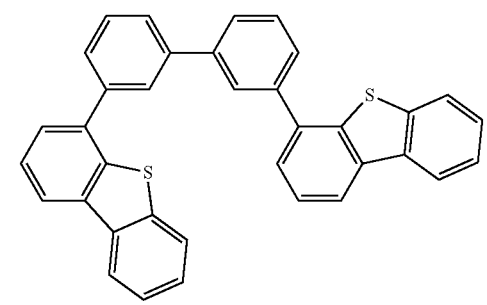 [SMILES: c1cc(-c2cccc(-c3cccc4c3sc3ccccc34)c2)cc(-c2cccc3c2sc2ccccc23)c1]

Hole Blocking Compound 1

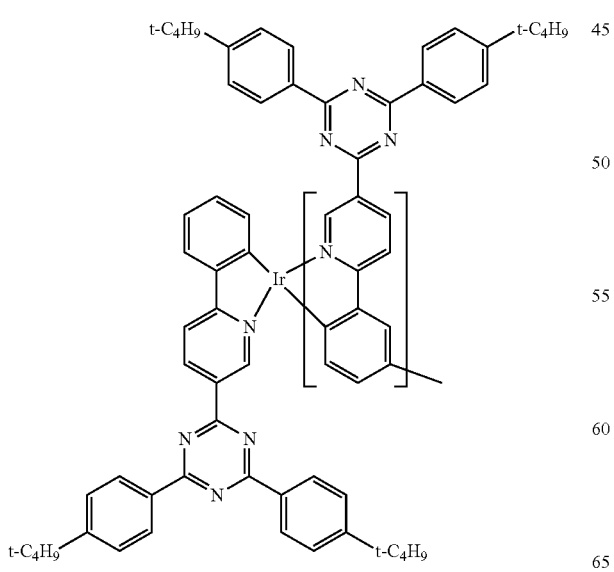

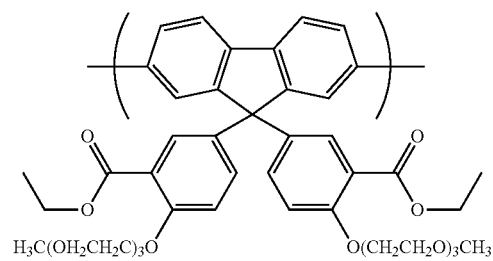

Electron-Transporting Unit 1
Comparative Device 1

A device was prepared as described for Device Example 1 except that Compound Example A was replaced with Comparative Compound 1.

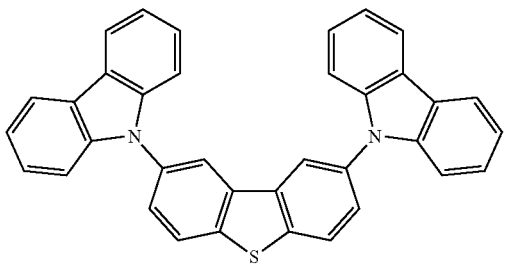 [SMILES: c1ccc2c(c1)c1ccccc1n2-c1ccc2sc3ccc(-n4c5ccccc5c5ccccc54)cc3c2c1]

Comparative Compound 1

Figure 2:
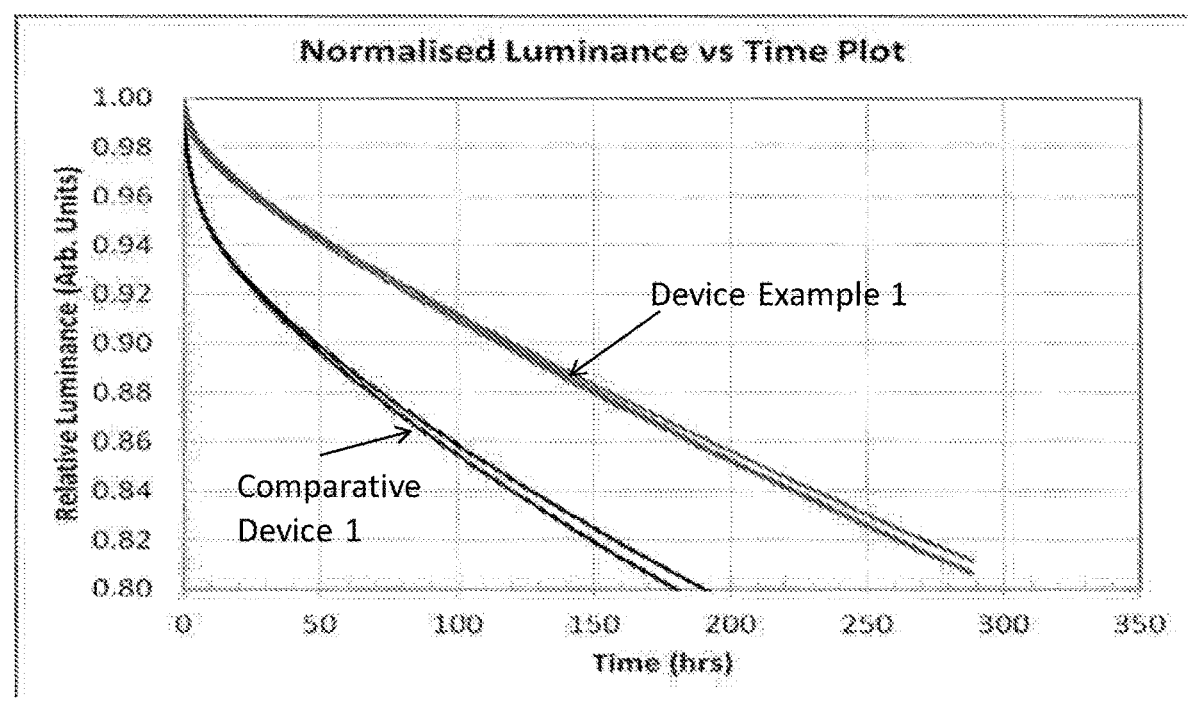
FIG. 2 is a graph of luminance vs. time for a device according to an embodiment of the invention and a comparative device.

With reference to FIG. 2, the time taken for the brightness of Device Example 1 to decay to 80% of a starting luminance is considerably longer than that of Comparative Device 1.

Although the present invention has been described in terms of specific exemplary embodiments, it will be appreciated that various modifications, alterations and/or combinations of features disclosed herein will be apparent to those skilled in the art without departing from the scope of the invention as set forth in the following claims.

The invention claimed is:

1. A compound of formula (I):

Z-Core-Z (I)

wherein:
Z in each occurrence is independently a group of formula (II):

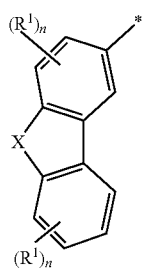

X is S or O;
$R^1$ independently in each occurrence is a substituent;
n is 0 or a positive integer;
-* is a direct bond to Core; and
Core is of formula (IIIb):

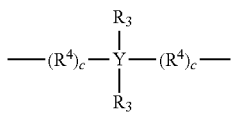

wherein
$R^3$ is a substituent;
$R^4$ is an arylene or heteroarylene group that may independently in each occurrence be unsubstituted or substituted with one or more substituents;
Y is C;
and
c is 1.

2. A compound according to claim 1 wherein each $R^4$ is a phenylene group that may be unsubstituted or substituted with one or more substituents.

3. A compound according to claim 1 wherein each $R^3$ is an aryl or heteroaryl group which may be unsubstituted or substituted with one or more substituents.

4. A compound according to claim 1 having a HOMO level of at least 5.8 eV from vacuum level as measured by square wave voltammetry.

5. A composition comprising a compound according to claim 1 and at least one light-emitting dopant.

6. A composition according to claim 5 wherein the light-emitting dopant is a phosphorescent dopant.

7. A composition according to claim 5 wherein the light-emitting dopant is a blue light-emitting material.

8. A composition according to claim 5 wherein the light-emitting dopant is a metal complex comprising at least one unsubstituted or substituted phenylimidazole or phenyltriazole ligand.

9. A formulation comprising a compound according to claim 1 and one or more solvents.

10. An organic light-emitting device comprising an anode, a cathode and a light-emitting layer between the anode and the cathode wherein the light-emitting layer comprises a compound according to claim 1.

11. An organic light-emitting device comprising an anode, a cathode and a light-emitting layer between the anode and the cathode wherein the organic light-emitting layer comprises a composition according to claim 5.

12. An organic light-emitting device according to claim 10 wherein the device comprises at least one further light-emitting layer.

13. An organic light-emitting device according to claim 10 wherein the device emits white light.

14. A method of forming an organic light-emitting device according to claim 10 comprising the step of forming the light-emitting layer over one of the anode and the cathode and forming the other of the anode and the cathode over the light-emitting layer.

15. A method according to claim 14 wherein the light-emitting layer is formed by depositing a formulation comprising the compound of formula (I) and one or more solvents and evaporating the one or more solvents.

16. A compound of formula (I):

Z-Core-Z (I)

wherein:
Z in each occurrence is independently a group of formula (II):

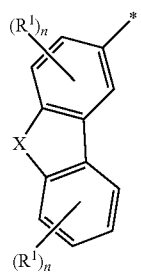

X is S or O;
R$^1$ independently in each occurrence is a substituent;
n is 0 or a positive integer;
-* is a direct bond to Core; and
Core is of formula (IIIb):

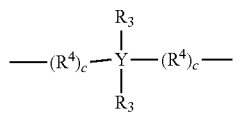
(IIIb)

wherein each R$^3$ is an aryl or heteroaryl group which may be unsubstituted or substituted with one or more substituents;

R$^4$ is an arylene or heteroarylene group that may independently in each occurrence be unsubstituted or substituted with one or more substituents;

Y is C; and c independently in each occurrence is 0 or a positive integer.

17. A composition comprising a compound according to claim 16 and at least one light-emitting dopant.

18. A formulation comprising a compound according to claim 16 and one or more solvents.

19. An organic light-emitting device comprising an anode, a cathode, and a light-emitting layer between the anode and the cathode, wherein the light-emitting layer comprises a compound according to claim 16.

20. A method of forming an organic light-emitting device according to claim 19 comprising the step of forming the light-emitting layer over one of the anode and the cathode and forming the other of the anode and the cathode over the light-emitting layer.

* * * * *